United States Patent [19]

Miyashita et al.

[11] 4,329,460
[45] May 11, 1982

[54] URACIL DERIVATIVES AND PRODUCTION THEREOF

[75] Inventors: Osamu Miyashita, Takatsuki; Koichi Matsumura, Ibaraki; Hiroshi Shimadzu, Settsu; Naoto Hashimoto, Suita, all of Japan

[73] Assignee: Takeda Chemical Industries, Ltd., Osaka, Japan

[21] Appl. No.: 48,169

[22] Filed: Jun. 13, 1979

Related U.S. Application Data

[63] Continuation of Ser. No. 780,683, Mar. 23, 1977, abandoned.

[30] Foreign Application Priority Data

| Mar. 31, 1976 | [JP] | Japan | 51-36653 |
| Oct. 27, 1976 | [JP] | Japan | 51-129932 |
| Dec. 6, 1976 | [JP] | Japan | 51-146795 |

[51] Int. Cl.$^3$ ............... A61K 31/515; C07D 239/22; C07D 401/04; C07D 401/06
[52] U.S. Cl. ............... 544/301; 424/248.54; 424/248.55; 424/251; 424/254; 544/123; 544/229; 544/302; 544/303; 544/311; 544/314; 544/317
[58] Field of Search ............... 544/301, 302, 303

[56] References Cited

U.S. PATENT DOCUMENTS

| 3,201,387 | 8/1965 | Heidelberger | 260/211.5 |
| 3,221,010 | 11/1965 | Duschinsky et al. | 424/251 |
| 3,360,523 | 12/1967 | Loux et al. | 424/251 |
| 3,466,280 | 9/1969 | Loux et al. | 424/251 |
| 3,775,406 | 11/1973 | Trueb et al. | 424/250 |
| 3,954,758 | 5/1976 | Schuman et al. | 424/251 |
| 3,954,759 | 5/1976 | Anderson et al. | 424/251 |
| 3,987,045 | 10/1976 | Bock et al. | 260/326.1 |
| 4,017,626 | 4/1977 | Gauri | 424/251 |
| 4,071,519 | 1/1978 | Ozaki et al. | 424/251 |
| 4,080,455 | 3/1978 | Yasumoto et al. | 424/251 |
| 4,088,646 | 5/1978 | Ishida et al. | 424/251 |

FOREIGN PATENT DOCUMENTS 1006155 9/1965 United Kingdom ............... 424/251

OTHER PUBLICATIONS

Johnson et al., J. Am. Chem. Soc., vol. 55, pp. 3781–3783, (1933).

Primary Examiner—Alton D. Rollins
Attorney, Agent, or Firm—Burgess, Ryan and Wayne

[57] ABSTRACT

New derivatives of the formula:

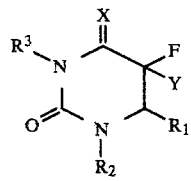

(wherein X is O or NH; $R_1$ is —OH which may optionally be etherified or esterified, etherified mercapto or —NH$_2$ which may optionally be substituted; $R_2$ and $R_3$, respectively, mean H, lower alkyl or

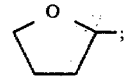

and Y is an esterified or amidated carboxyl group, or CN). These derivatives are produced, by fluorination of corresponding 1,2,3,4-tetrahydro-2,4-dioxopyrimidine compounds and can be converted into 5-fluorouracil derivatives under hydrolytic conditions. The new derivatives are able to prolong the lives of animals having carcinomas or have antiviral activity.

62 Claims, No Drawings

URACIL DERIVATIVES AND PRODUCTION THEREOF

This is a continuation, of application Ser. No. 780,683, filed Mar. 23, 1977, now abandoned.

This invention relates to novel compounds having the formula:

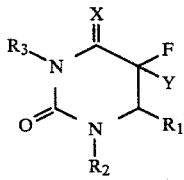

(I)

(wherein X is O or NH; $R_1$ is hydroxyl group which may optionally be etherified or esterified, esterified mercapto or an amino group which may optionally be substituted; $R_2$ and $R_3$, respectively, mean H, lower alkyl or

and Y is an esterified or amidated carboxyl group, or CN) as well as to a method for producing the same compounds. Compounds (I) are able to prolong the lives of animals having carcinomas and/or have antiviral activity, to name but a few of their useful properties.

Further, this invention relates to a novel and useful method for producing a compound of the general formula:

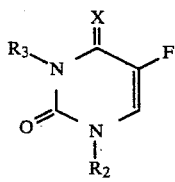

(VIII)

(wherein X, $R_2$ and $R_3$ have the same meanings as respectively defined hereinbefore).

The compounds (VIII) includes, for instance, 5-fluorouracil and 5-fluoro-1-(2-tetrahydrofuryl)uracil both of which are of value as carcinostatic agents.

It is an object of this invention to provide novel compounds (I) and methods for producing thereof.

Another object of this invention is to provide a novel method of producing the compound of the general formula (VIII).

This invention is directed to the compound (I) which can be produced, for instance, by the methods described hereinafter.

(1) A method for producing a compound of the formula:

(III)

(wherein X is O or NH; $R_{1-i}$ is a hydroxy group which may optionally be etherified or esterified, or an amino group which may be substituted; $R_2$ and $R_3$, respectively, mean H, lower alkyl or

and Y is an esterified or amidated group, or CN) which comprises fluorinating a compound of the formula:

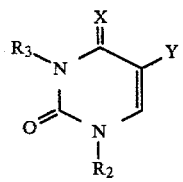

(II)

(wherein all the symbols have the same meanings as defined above) in the presence of water, an alcohol or a carboxylic acid.

(2) A method for producing a compound of the formula;

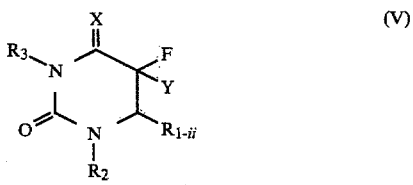

(V)

(wherein X is O or NH; Y is an esterified or amidated carboxyl group or CN; $R_{1-ii}$ is an etherified hydroxyl or mercapto group or an amino group which may optionally be substituted; and $R_2$ and $R_3$, respectively mean H, lower alkyl or

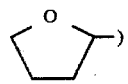

)

which comprises subjecting a compound of the formula:

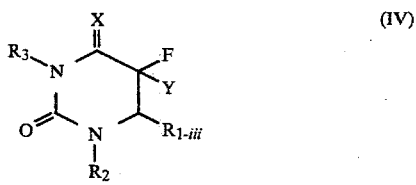

(IV)

(wherein $R_{1-iii}$ is a hydroxyl or mercapto group which may optionally be etherified or esterified; and other symbols have the same meanings as defined above) to etherification, thioetherification or amination.

(3) A method for producing a compound of the formula:

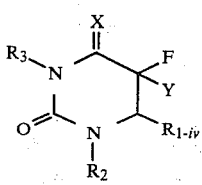

(VII)

(wherein X is O or NH; Y is an esterified or amidated carboxyl group, or CN; $R_{1\text{-}iv}$ is an esterified hydroxyl group; and $R_2$ and $R_3$, respectively, mean H, lower alkyl or

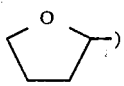

)

which comprises esterifying a compound of the formula:

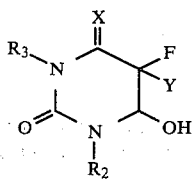

(VI)

(wherein all the symbols have the same meanings as defined above)

The esterified carboxyl group Y may be represented by the formula COOY′ where Y′ may for example be an acyclic or cyclic alkyl group of 1 to 18 carbon atoms (for example, methyl, ethyl, propyl, isopropyl, isobutyl, sec-butyl, cyclobutyl, penyl, cyclopentyl, hexyl, cyclohexyl, heptyl, octyl, octadecyl, cyclopropylmethyl, 2-cyclopropylethyl, 2-methylcyclohexyl, etc.) or alkenyl (e.g. allyl). These alkyl groups may be substituted, for example, by halogen, alkoxy (2-chloroethyl, 2,2,2-trifluoroethyl, 2-ethoxyethyl, etc.). And Y′ may also be an aralkyl group of 7 to 8 carbon atoms (for example, benzyl, phenethyl) or an aryl group of 6 to 8 carbon atoms (for example, phenyl, o-,m-,p-cresyl, o-,m-,p-chlorophenyl, 2,3-, 2,4-, 3,5-dimethylphenyl).

The amidated carboxyl group Y may for example be an unsubstituted amido group or a mono- or di-substituted amido group. For example, there may be mentioned a carboxyl group amidated by an amine which is mono- or di-substituted with, for example, alkyl(s) having 1 to 8 carbon atoms (e.g. methyl, ethyl, and propyl, butyl, pentyl, hexyl and octyl, and isomers thereof), alkyl(s) such as above and substituted by hydroxyl, halogen or cycloalkyl (e.g. 2-hydroxyethyl, 2-chloroethyl, cyclopropylmethyl, etc.). There may also be mentioned a carboxyl group amidated by an amine which is mono- or di-substituted with cycloalkyl(s) (e.g. cyclobutyl, cyclopentyl, cyclohexyl, etc.), aralkyl(s) (e.g. benzyl, phenethyl, etc.), aromatic group(s) having 6 to 8 carbon atoms (e.g. phenyl, o-, m-, p-tolyl, o-, m-, p-methoxyphenyl, o-, m-, p-ethoxyphenyl, o-, m-, p-chlorophenyl, o-, m-, p-fluorophenyl, o-, m-, p-trifluoromethylphenyl, 2,3-, 3,4-, 3,5-xylyl, etc.). Y may further be a carboxyl group amidated by nitrogen-containing heterocyclic amines having 2 to 5 carbon atoms (e.g. aziridine, azetidine, pyrrolidine, piperidine, morpholine, N′-methylpiperazine, etc.). As the etherified hydroxyl groups $R_1$, $R_{1\text{-}i}$, $R_{1\text{-}ii}$, $R_{1\text{-}iii}$, there may be mentioned alkoxy or cycloalkoxy group of 1 to 18 carbon atoms (e.g. methoxy, ethoxy, and propoxy, butoxy, pentyloxy, hexyloxy, heptyloxy, octyloxy, decyloxy and octadecyloxy as well as isomers thereof, cyclopropylmethoxy, cyclobutyloxy, cyclopentyloxy, cyclohexyloxy, 2-methylcyclohexyloxy), substituted alkoxy group (e.g. hydroxyethoxy, chloroethoxy, methoxyethoxy, ethoxyethoxy, trifluoroethoxy), alkenyloxy (e.g. allyloxy, cyclohexenyloxy), alkynyloxy (e.g. propargyloxy, 3-butynyloxy, 2-butynyloxy), aralkyloxy (e.g. benzyloxy, p-chlorobenzyloxy, p-fluorobenzyloxy, phenethyloxy), aryloxy group of 6 to 8 carbon atoms (e.g. phenoxy, o-, m-, p-tolyloxy, o-, m-, p-chlorophenoxy, 2,3-, 2,4-, 3,5-dimethylphenoxy, o-, m-, p-methoxyphenoxy, o-, m-,p-ethoxyphenoxy, p-fluorophenoxy, o-, m-, p-trifluoromethylphenoxy), etc. As the etherified mercapto groups $R_1$, $R_{1\text{-}ii}$, and $R_{1\text{-}iii}$, there may be mentioned the etherified mercapto groups corresponding to the above-mentioned etherified hydroxyl groups as well as β-naphthylmercapto.

As the esterified hydroxyl groups $R_1$, $R_{1\text{-}i}$, $R_{1\text{-}iii}$ and $R_{1\text{-}iv}$, there may be mentioned aliphatic acyloxy group having 1 to 4 carbons (e.g. formyloxy, acetyloxy, propionyloxy, butyryloxy, isobutyryloxy, trifluoroacetyloxy, trichloroacetyloxy, dichloroacetyloxy, monochloroacetyloxy, etc.), aromatic acyloxy group (e.g. benzoyloxy, p-methylbenzoyloxy, p-chlorobenzoyloxy, p-methoxybenzoyloxy, etc.), aromatoaliphatic acyloxy group (e.g. phenylacetyloxy), and sulfonyloxy group (e.g. p-toluenesulfonyloxy, methanesulfonyloxy).

The substituted amino groups $R_1$ and $R_{1\text{-}ii}$ are mono- or di-substituted amino groups, the substituents being exemplified by alkyls of 1 to 7 carbon atoms (e.g. methyl, ethyl, propyl, isopropyl, and butyl, pentyl and hexyl as well as their isomers, cyclopropylmethyl, allyl, ethoxycarbonylmethyl), aralkyl groups (e.g. benzyl, phenethyl), cycloalkyl groups (e.g. cyclopropyl, cyclobutyl, cyclopentyl, cyclohexyl), phenyl and phenyl groups substituted by lower alkyls (e.g. methyl, ethyl) or lower alkoxy groups. The 4- to 6-membered nitrogen-containing heterocyclic groups (e.g. azetidino, pyrrolidino, piperidino, morpholino, piperazino) are also included in the category of substituted amino groups $R_1$ and $R_{1\text{-}ii}$. As examples of the substituted amino groups $R_1$ and $R_{1\text{-}ii}$, there may be mentioned methylamino, ethylamino, propylamino, butylamino, pentylamino, hexylamino, allylamino, ethoxycarbonylamino, cyclopropylmethylamino, cyclobutylamino, cyclopentylamino, cyclohexylamino, dimethylamino, diethylamino, di-n-propylamino, di-isopropylamino, benzylamino, phenethylamino, anilino, toluidino and anisidino.

The lower alkyl groups $R_2$ and $R_3$ may each be methyl, ethyl, propyl, isopropyl, butyl or isobutyl, for instance.

Since the compound (I) of the invention has asymmetric carbons at the 5- and 6-positions, there can exist two isomers which have a hydrogen atom in cis- or trans-configuration to the fluorine atom at 5-position and, with respect to the each isomer, there can exist d- or l-form of optical isomers. Therefore, the compound (I) includes each of the isomers and a mixture of at least two kinds of the isomer.

The processes according to this invention will be described hereinafter in detail.

The process for production of the compound (III) by fluorination of the compound (II):

The compound (III) is produced by fluorinating the compound (II) in the presence of water, an alcohol or a carboxylic acid. As examples of the alcohol employable in this reaction, there may be mentioned alkanols or cycloalkanols of 1 to 8 carbon atoms (e.g. methanol, ethanol and propanol, butanol, pentanol, hexanol and octanol as well as isomers thereof, cyclopentanol and cyclohexanol) and substituted alkanols (e.g. trifluoroethanol, trichloroethanol, ethylene glycol, trimethylene glycol, epichlorohydrin, ethylene glycol monomethyl ether, ethylene glycol monoethyl ether, diethylene glycol monomethyl ether, diethylene glycol monoethyl ether, etc.).

As to the carboxylic acid employable for the purposes of this reaction, there may be mentioned carboxylic acids having up to 4 carbon atoms (e.g. acetic acid, propionic acid, butyric acid, isobutyric acid, cyclopropane-carboxylic acid, cyclobutanecarboxylic acid) and their corresponding halogen-substituted carboxylic acids (e.g. trifluoroacetic acid, pentafluoropropionic acid), for instance.

The water, alcohol or carboxylic acid employable for the purposes of this reaction may also be allowed to function as the solvent as well.

In this reaction, the residual part of the molecule formed by substracting H from the OH group in the molecule of the water, alcohol or carboxylic acid employed, is introduced into the compound (III) as $R_{1-i}$.

Where the reaction is carried out in the presence of a mixture of two or more of water, alcohol and carboxylic acid, there may be produced a mixture of the compounds (III) carrying different residues as $R_{1-i}$ or one of the possible compounds (III) as a predominant product.

This fluorination reaction may be conducted by means of a fluorinating agent. As examples of said fluorinating agent there may be mentioned fluorosulfurhypofluorites such as pentafluorosulfurhypofluorite; fluoro-loweralkylhypofluorites of 1 to 6 carbon atoms such as trifluoromethylhypofluorite, perfluoropropylhypofluorite, perfluoroisopropylhypofluorite, perfluoro-tert-butylhypofluorite, monochlorohexafluoropropylhypofluorite and perfluoro-tert-pentylhypofluorite, etc.; and difluoroxy compounds such as 1,2-difluoroxydifluoroethane and difluoroxydifluoromethane. Molecular fluorine may also be employed with success. Where a gaseous fluorinating agent such as molecular fluorine is employed, it is preferably diluted with an inert gas such as nitrogen or argon before being introduced into the reaction system. Among preferred fluorinating agents there are fluorine gas and trifluoromethylhypofluorite. The fluorinating agent may be employed in the proportion of 1 to about 10 molar equivalents, preferably about 1.1 to 4 molar equivalents, more preferably about 1.2 to 2.5 molar equivalents, based on the compound (II).

The reaction temperature may be within the range of about −78° C. to +40° C., preferably within the range of about −20° C. to +30° C., more preferably within the range of about +14° C. to +30° C.

The compound (III) produced in the above manner can be easily separated from the reaction mixture in a manner conventional per se. For example, the compound (III) can be recovered by stripping off the solvent under reduced pressure. An alternative procedure which is practicable in certain cases comprises adding a reducing agent (e.g. $NaHSO_3$) to the reaction mixture to remove the oxidative by-product, neutralizing the reaction mixture with $NaHCO_3$, $CaCO_3$ or $MgCO_3$, filtering it to remove the insolubles and removing the solvent form the filtrate by distillation under reduced pressure. The product thus obtained may be further purified by any of the routine procedure (e.g. recrystallization, chromatography on silica gel or alumina, etc.).

Thus, 5-fluoro-pyrimidine derivatives are obtained and, by the procedure similar to that above mentioned, the corresponding 5-chloro-pyrimidine derivatives can be produced employing a chlorinating agent instead of the fluorinating agent.

As the chlorinating agent, there may be employed, among others, such agents as molecular chlorine, hydrochloric acid-hydrogen peroxide, hypochlorous acid, tert-butyl hypochlorite and other alkylhypochlorites, nucleophilic chlorinating agents such as N-chlorosuccinimide, or any of the reagents that will react with water or an alcohol to yield one of said agents in the reaction mixture (in situ). Particularly preferred are the reagents comprising a combination of molecular chlorine with water or alcohol. In such instances, the chlorination reaction may be easily carried out by bubbling chlorine gas into a solution or dispersion of compound (II) in the reaction medium containing water or alcohol.

Another part of the present invention is directed to a method for producing a compound of the formula:

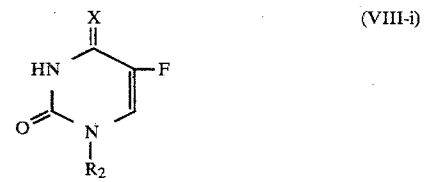

(VIII-i)

(wherein X is a member of the group consisting of O and NH; and $R_2$ is a member of the group consisting of H, a lower alkyl and

)

which comprises treating a compound of the formula:

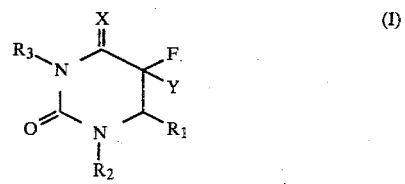

(I)

(wherein Y is a member of the group consisting of an esterified carboxyl, an amidated carboxyl and CN; $R_1$ is a member of the group consisting of hydroxyl ethers and esters, and amino which may optionally be substituted; $R_3$ is a member of the group consisting of H and

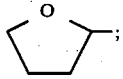

and X and R$_2$ have the same meanings as defined above) under hydrolytic conditions.

Thus, the compound (VIII-i) may be produced by treating the compound (I) with an acid or base under mild conditions.

The acids useful for this purpose include mineral acids, such as hydrochloric acid, hydrofluoric acid, sulfuric acid, phosphoric acid, nitric acid, etc, or organic strong acids, such as trifluoroacetic acid, trifluoromethanesulfonic acid, etc. Normally, the compound (I) is dissolved in an aqueous solution of such an acid.

Concentration of the acid may be selected generally from the range of about 0.05 to 10 normal, and preferably about 0.5 to 4 normal for the production of the compound (VIII-i) where X is O and R$_2$ is H, and preferably about 0.1 to 1 normal for the production of the compound (VIII-i) where X is O and R$_2$ is

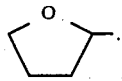

The reaction temperature may be selected generally from the range of about 0° C. to 110° C., preferably about 50° C. to 110° C. for the production of the compound (VIII-i) where X is O and R$_2$ is H, and preferably about 0° C. to 15° C. for the production of the compound (VIII-i) where X is O and R$_2$ is

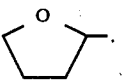

While the concentration of the acid in the medium is preferably as low as mentioned above, a comparatively large excess of acid may be employed as a whole with respect to compound (I). For example, the acid is used in the range of about 10 to 1000 molar equivalents and, normally, about 200 to 500 molar equivalents for the production of the compound (VIII-i) where X is O and R$_2$ is

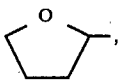

and normally, about 10 to 100 molar equivalents for the compound (VIII-i) where X is O and R$_2$ is H, based on the compound (I).

The progress of the reaction may be monitored by determination of the UV spectrum and thin-layer chromatogram of the reaction mixture.

The compound (VIII-i) is isolated and purified by using appropriately conventional procedure such as neutralization, extraction, recrystallization or chromatography.

The above treatment under acidic conditions may at times prove advantageous particularly with the compounds (I) wherein Y is an esterified carboxyl group, R$_1$ is an etherified or free hydroxyl group, R$_2$ is hydrogen or

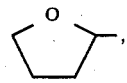

and R$_3$ is hydrogen. Especially the treatment under acidic conditions is most preferable for the production of the compound (VIII-i) where X is O and R$_2$ is H.

As mentioned before, the compound (VIII-i) is also produced by treating the compound (I) under hydrolytic conditions with base. As the base usable for this purpose may be mentioned an aqueous solution of an alkali hydroxide or alkali carbonate such as sodium hydroxide, potassium hydroxide, sodium carbonate, potassium carbonate, ammonia, triethylamine, etc. While the reaction proceeds satisfactorily at room temperature in a short period of time, there are cases in which the reaction mixture may be heated at about 50° C. to 70° C. After the reaction has been completed, the reaction mixture is neutralized, or made acidic if necessary, and the desired compound is isolated by extraction following removal of the solvent or by such other routine procedures as chromatography on activated carbon, or on suitable resins.

The treatment under basic hydrolytic conditions is particularly advantageous for the production of the compound (VIII-i) where X is O and R$_2$ is H or

from the compound (I) where X is O, Y is an esterified carboxyl, R$_1$ is an etherified hydroxyl or mono- or di-substituted amino group, R$_2$ is H or

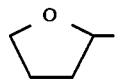

and R$_3$ is H. The treatment with a base is also applicable advantageously for the production of the compound (VIII-i) where X is O and R$_2$ is

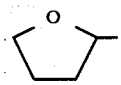

from the compound (I) where X is O, Y is an esterified carboxyl group, R$_1$ is an esterified hydroxyl group, R$_2$ is

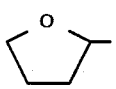

and R$_3$ is H.

The production of compound (VII) by esterification of compound (VI):

This esterification reaction may be successfully accomplished by a procedure known for the esterification or acylation of alcohols or phenols.

By way of illustration, one may employ the process which comprises reacting a compound (VI) with an esterifying or acylating agent adapted to introduce an esterified hydroxyl group corresponding to $R_1$-iv in the presence of an organic base (such as a tertiary base, e.g. pyridine, triethylamine, N-methylmorpholine, N,N-dimethylaniline, etc.). As examples of said esterifying or acylating agent may be mentioned the carboxylic acid halides (e.g. chloride, bromide) and anhydrides corresponding to $R_1$-ivH. More specifically, there may be mentioned acetyl chloride, acetyl bromide, n-propionyl chloride, n-butyryl chloride, cyclobutanecarbonyl chloride, benzoyl chloride, acetic anhydride, acetic formic anhydride, n-propionic anhydride, n-butyric anhydride, trifluoroacetic anhydride, monochloroacetic anhydride, benzoic anhydride, methanesulfonyl chloride, toluenesulfonyl chloride, etc. The amount of esterifying or acylating agent may be selected for example from the range of 1 to about 10 molar equivalents based on the compound (VI) and, preferably, from the range of about 2 to 7 equivalents on the same basis. There are instances in which the reaction may be conducted with success under ice-cooling at the one extreme to about 120° C. at the other extreme, preferably at a temperature within the range of about 5° to 80° C.

The compound (VII) produced in the above manner can be isolated by a known procedure. In a typical isolation and purification procedure, the reaction mixture is concentrated under reduced pressure to remove the solvent, etc. and, after washing with a suitable solvent such as ether, the residue is recrystallized or chromatographed on a column of silica gel.

The compound (VII) obtained in the above manner may be reconverted to the original starting compound (VI) either by hydrolysis in a neutral or weakly alkaline aqueous medium or by passing through a bed of moist alumina or silica gel.

The process for production of compound (V) by etherification, thioetherification or amination of compound (IV):

The compound (V) can be produced by reacting a compound (IV) with an alcohol, thiol or primary or secondary amine which may be represented by $R_{1-ii}H$. This reaction is generally known as nucleophilic substitution reaction and the nucleophilic reagent $R_{1-ii}H$ can be selected from a broad range of compounds carrying an active hydrogen atom.

As examples of the alcohol employable in this reaction may be mentioned alcohols of 1 to 18 carbon atoms (e.g. methanol, ethanol, 2,2,2-trifluoroethanol, and propanol, butanol, amyl alcohol, hexanol, cyclohexanol, octanol, decyl alcohol, octadecyl alcohol as well as their isomers), aralkyl alcohols of 7 to 8 carbon atoms (e.g. benzyl alcohol, phenethyl alcohol, o-, m-, p-anise alcohol, o-, m-, p-chloro- or fluorobenzyl alcohol, aromatic alcohols of 6 to 10 carbon atoms (e.g. phenol, o-, m-, p-cresol, o-, m-, p-chlorophenol α- and β-naphthol, alkenyl alcohols (e.g. ally alcohol), alkynyl alcohols (e.g. propargyl alcohol), etc.

As examples of the thiol employable for the purposes of this thioetherification, there may be mentioned the thiols corresponding to the above-mentioned alcohols. There are cases in which said etherification or thioetherification may be accomplished with advantage in the presence of an acid catalyst (e.g. inorganic and organic strong acids, e.g. hydrogen chloride, anhydrous hydrogen fluoride, concentrated sulfuric acid, methanesulfonic acid, p-toluenesulfonic acid, trifluoroacetic acid, etc.; Lewis acids, e.g. borontrifluoride, zinc chloride, titanium chloride, etc.).

The etherification and thioetherification may be conducted in the presence of a solvent. The solvent may be the alcohol or thiol which is employed as the etherification or thioetherification reagent, although use may as well be made of other solvents such as halogenated hydrocarbons (e.g. dichloromethane, chloroform, carbon tetrachloride, tetrachloroethane, trichlorofluoromethane), ethers (e.g. ethyl ether, dioxane, tetrahydrofuran, 1,2-dimethoxyethane), aromatic hydrocarbons, (e.g. benzene, toluene, xylene, chlorobenzene), etc.

There are cases in which this etherification or thioetherification may be conducted with advantage while removing the by-product water, alcohol or the like by a conventional procedure or means such as azeotropic distillation, silica gel, molecular sieve, $Na_2SO_4$ or $MgSO_4$. It should be understood that, in the course of this etherification reaction, where Y is an esterified carboxyl group, a transesterification may take place at Y and where Y is a cyano group, it may be converted to an esterified carboxyl group.

As examples of the primary or secondary amine employable for the purposes of said amination reaction, there may be mentioned the amines corresponding to $R_{1-ii}H$. While the amination reaction may be conducted in the same manner as said etherification and thioetherification, $R_{1-iii}$ in starting compound (IV) is preferably an acyloxy group. While the etherification, thioetherification and amination reaction may each proceed satisfactorily at room temperature, the reactions may be conducted under heating at a temperature not exceeding about 120° C.

After the reaction has been completed, the compound (V) thus produced can be isolated and purified from the reaction mixture by a procedure known per se. For example, the solvent may be distilled off under reduced pressure to recover the desired compound and the latter may be further purified by recrystallization or chromatography.

The starting compound (II) employable in the production method according to this invention can be easily produced by known processes, for examples the methods described in the following literature, or by methods analogous thereto.

(1) C. W. Whitehead, J. Am. Chem. Soc., 74, 4267(1952)

(2) H. L. Wheeler, T. B. Johnson, C. O. Johns, Am. Chem. J., 37 392(1907)

(3) V. G. Nemets, B. A. Ivin., Zhurnal Obshchei Khimii, 35, 1299(1965)

(4) J. Klosa, J. Pr. Chem., 26 43(1964)

(5) T. B. Johnson, Am. Chem. J. 42, 514(1909)

(6) M. Prystaś, F. Šorm, Collect. Czech, Chem. Comm. 31 3990(1966)

(7) T. L. V. Ulbricht, T. Okuda, C. C. Price, Org, Synth. Coll. Vol. 4, 566(1963)

It has also been found that a compound of the following formula:

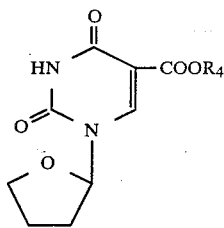

(IX)

($R_4$ is a lower alkyl group) which is included in the starting compounds of this invention may be produced in very high yield by the steps of silylating a compound of the formula;

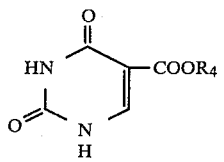

(X)

($R_4$ is as defined above) with a silylating agent to produce a bis-silyl compound of the formula;

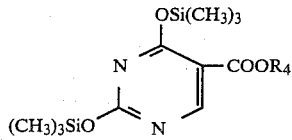

(XI)

($R_4$ is as defined above) and reacting the compound (XI) with 2-chlorotetrahydrofuran or with 2,3-dihydrofuran in the presence of hydrogen chloride.

The lower alkyl represented by $R_4$ may be those having up to 4 carbon atoms (e.g. methyl, ethyl, propyl, isopropyl as well as butyl and isomers thereof.

The afore-mentioned silylation may be carried out in a routine manner. For example, a bis-silyl compound of compound (X) may be produced by reacting compound (X) with trimethylsilyl chloride in the presence of a base (e.g. triethyl amine, pyridine) or with hexamethyldisilazane in the presence of a catalyst (e.g. trimethylsilyl chloride or ammonium sulfate).

The reaction of such a bis-silyl derivative with 2-chlorotetrahydrofuran or with 2,3-dihydrofuran in the presence of hydrogen chloride may be conducted at a temperature in the range of about −78° C. to +100° C., preferably at about −70° C. to +40° C. and, for still better results, at about −20° C. to +30° C., either in the presence or absence of a solvent (e.g. an aprotic solvent such as 1,2-dimethoxyethane, dimethylformamide, methylene chloride or acetonitrile).

The compound (IX) may also be produced by reacting the compound (X) with 2,3-dihydrofuran in a closed reaction vessel.

Where one of the starting materials, i.e. 2,3-dihydrofuran, is employed in large excess, this reaction does not necessarily require the use of a solvent. However, the reaction normally proceeds with advantage in the presence of a solvent in many cases where an equivalent or slight excess mole of 2,3-dihydrofuran is employed to each mole of compound (X). The solvent is preferably one of high polarity in view of the solubility factor of the pyrimidine base. Thus, for example, acid amides (e.g. dimethylformamide, dimethylacetamide, formamide or hexamethylphosphoramide), esters (e.g. methyl formate, ethyl formate) and tertiary amines (e.g. triethylamine, pyridine) as well as suitable mixtures of such solvents.

The reaction temperature may be normally selected from within the range of about 120° C. to 200° C., preferably about 130° C. to 190° C., although it may be higher or lower than said range. While the reaction time depends upon other conditions, it may be selected normally from the range of about 2 to 24 hours.

The compound (X) may be easily produced, for example by the method described in Journal of the American Chemical Society 74, 4267(1952) or a process analogous thereto.

The compounds (I) are of value as they not only display potent inhibitory activity against the growth and multiplication of tumorous cells, for example in KB-cell line (the cultured cells derived from human carcinoma of nasopharynx), C-34 cell line (the fibroblast cells of mouse kidney) and AC-cell line (the astrocytoma cells of rat) but also exert an eminent life span-prolonging action upon mice with leukemia (P-388, L-1210). The compounds (I) inhibit growth and multiplication of various tumorous cells in mammals (such as rats, mice and human beings) and have a life prolonging effect upon such mammals with leukemia. The compounds (I) may each be orally or non-orally administered as they are or, as formulated with a pharmacologically acceptable carrier, excipient or diluent in the routine manner, in such dosage forms as powders, granules, dry syrup, tablets, capsules, suppositories and injections. Depending upon the species of animal, disease and symptoms that must be managed, the particular compound, route of administration, etc., the dosage is normally selected from within the range of about 25 to 800 mg/kg body weight daily. While the upper limit is about 400 mg/kg body weight, more preferably about 200 mg/kg in many cases, there may be cases in which a higher or lower dose level is desirable.

The compounds (I) transfer into blood in a considerable high concentration, which may be maintained for a prolonged period.

Generally from the view point of pharmacological properties including toxicity, the compounds (I) are preferable where X is O, Y is an esterified carboxyl group, $R_1$ is an etherified hydroxyl group, $R_2$ is H or

and $R_3$ is H, and are more preferable where X is O, Y is an esterified carboxyl group of 2 to 9 carbon atoms, $R_1$ is an etherified hydroxyl group of 1 to 12 carbon atoms, $R_2$ is H or

and $R_3$ is H, and are most preferable where X is O, Y is an esterified carboxyl group of 2 to 5 carbon atoms, $R_1$ is an etherified hydroxyl group of 1 to 8 carbon atoms and both $R_2$ and $R_3$ are H.

(1) The procedure of a test on the life-prolonging effect upon leukemia P 388 in mice One tenth ml of diluted ascitic fluid containing 1×10⁵ cells was implanted in BDF₁ mice weighing 18 to 25 g. A suspension of the test-compound is injected intraperitoneally at a constant rate of volume of 0.1 ml/10 g body weight. As the detailed experimental method, the Protocols for Screening Chemical Agents (Geran, R. I., Greenberg, N. H., Macdonald, M. M., Schumacher, A. M., and Abbott, B. J.: Protocols for Screening Chemical Agents and Natural Products against Animal Tumors and Other Biological Systems. Cancer Chemotherapy Rept., 3 (Part 3) 7, 1972) is adopted.

The results are recorded in compliance to the T/C % value calculated on the basis of the median survival time of treated to control animals.

Test Results:

| Compound | Dose (mg/kg/day) | T/C(%) |
|---|---|---|
| Methyl 5-fluoro-6-methoxy-1,2,3,4,5,6-hexahydro-2,4-dioxopyrimidine-5-carboxylate | 200 | 243 |
| | 100 | 217 |
| | 50 | 208 |
| Ethyl 6-ethoxy-5-fluoro-1,2,3,4,5,6-hexahydro-2,4-dioxopyrimidine-5-carboxylate | 200 | 160 |
| | 100 | 143 |
| | 50 | 130 |

(2) Inhibitory effects upon the multiplication of tumorous cells

Test procedure:

(1) Inhibition of KB cell multiplication

2×10⁴ cells were suspended in 1 ml of Eagle's Minimal Essential Medium (MEM)+10% fetal calf serum (MEM.10 Fcs) and seeded in a glass dish (d=1.8 cm) containing a round coverslip (d=1.5 cm).

On the first day after seeding, three coverslips (per test group) were taken out and transferred to a single glass dish (d=4.5 cm) holding 5 ml of MEM.10 Fcs containing a verying concentration of the compound. On the 4th day after seeding, the number of cells per coverslip (3 slips for each concentration level) was determined with a Coulter counter. The result was expressed in the concentration of the drug giving a cell count of 50% ($ED_{50}$) with the average number of cells for the control (not medicated) group on the 4th day being taken as 100%.

(2) Inhibition of the induction of cell multiplication in BAV3-infected C34 cells 1×10⁵ cells were suspended in 1 ml of Eagle's MEM+10% fetal calf serum (MEM.10 Fcs) and seeded in a glass dish (d=1.8 cm) containing a round coverslip (d=1.5 cm).

On the 2nd day after seeding, infection (37° C., 120 min.) (mock-infection or virus infection; in the case of the latter, multiplicity of infection per cell=100−200 PFU/cell) was carried out. After this operation, one test group (3 coverslips) was taken out and transferred to a glass dish (d=4.5 cm) holding 5 ml of MEM.2 Fcs containing each concentration of compound.

On the 6th day after seeding, the number of cells per coverslip was determined with a Coulter counter. For each experimental group, the difference in all members between virus-infected cells (V) and mock-infected cells (M) was calculated. The result was expressed in the concentration of the drug giving a (V-M) value of 50% ($ED_{50}$) for the control (not medicated) group as 100%.

(3) Inhibition of Ac cell multiplication

1×10⁵ AC cells (2 ml of Eagle's MEM, with 10% fetal calf serum were seeded in a Falcon dish (in. diam. 3.5 cm). On the 24th hour, replacement was made with the above culture medium containing a varying concentration of drug. The number of cells was determined on the 3rd day following the replacement of medium. The pharmacologic effect was expressed in $ED_{50}$ (the concentration of the drug giving a cell count of 50% for the treated group with the number of cells for the control group being taken as 100%.

Test Results:

| Compound | Inhibition of cell growth | $ED_{50}$ (γ/ml) |
|---|---|---|
| Methyl 5-fluoro-6-methoxy-1,2,3,4,5,6-hexahydro-2,4-dioxopyrimidine-4-carboxylate | KB | 3 |
| | AC | 0.12 |
| | BAV3-infected C34 | 0.023 |
| Ethyl 5-fluoro-6-ethoxy-1,2,3,4,5,6-hexahydro-2,4-dioxopyrimidine-5-carboxylate | KB | 2.8 |
| | BAV3-infected C34 | 0.023 |

EXAMPLE 1

In 400 ml. of water is suspended 15.04 g. (80 mmoles) of methyl 1,2,3,4-tetrahydro-2,4-dioxopyrimidine-5-carboxylate monohydrate and the suspension is stirred vigorously at room temperature. Then, a current of fluorine gas previously diluted with nitrogen to a fluorine-to-nitrogen ratio of 1:3 (V/V) is passed through the suspension at the rate of about 45 ml. per minute over a period of 6.6 hours, during which the reaction system is cooled with water from time to time so that the reaction temperature will not exceed 28° C. (fluorine consumption=1.95 molar equivalents). While the reaction mixture is cooled, 15.6 g. of calcium carbonate is then added to neutralize the hydrogen fluoride. Following the addition of 5.2 g. of sodium hydrogen sulfite, the insolubles are filtered off and the filtrate is concentrated under reduced pressure. The residue is dried in vacuo to recover 23.7 g. of a powder. To the powder is added 500 ml. of acetone and following removal of the insolubles by filtration, the acetone is distilled off under reduced pressure. The residue is purified by column chromatography on silica gel (solvent:acetone—chloroform=1:3 (V/V) to obtain 13.0 g. of methyl 5-fluoro-6-hydroxy-1,2,3,4,5,6-hexahydro-2,4-dioxopyrimidine-5-carboxylate. melting point: 171°–172° C. NMR spectrum (DMSO-d₆) δ: 3.80(3H,s), 4.90(1H,m; after addition of deuterium oxide d, $J_{HF}=4H_Z$), 7.13(1H, d, J=5H$_Z$), 8.53(1H, broad), 10.85(1H, broad).

Elemental analysis for C₆H₇FN₂O₅: Calcd.: C, 34.96; H, 3.42; N, 13.59. Found: C, 35.07; H, 3,41; N, 13.58.

EXAMPLE 2

In a pressure-resistant glass tubular reactor of 100 ml. capacity, 510 mg. (3.0 mmoles) of methyl 1,2,3,4-tetrahydro-2,4-dioxopyrimidine-5-carboxylate is suspended is 20 ml. of water and frozen in a dry ice-ethanol bath. To this is added 20 ml. of fluorotrichloromethane in the above cooling bath, and trifluoromethylhypofluorite (about 400 mg.) is dissolved therein. After closing the reactor tightly, the cooling bath is removed and the reactor is allowed to return to room temperature.

The material swiftly reacts and dissolves in the water. As the reaction mixture is stirred overnight, the solids disappear. The excess trifluoromethylhypofluorite is removed by passage of nitrogen gas, and following addition of anhydrous sodium acetate (400 mg.), the solution is concentrated to dryness under reduced pressure. The resultant solid is washed with acetone. The acetone solution is concentrated under reduced pressure to give 700 mg. of methyl 5-fluoro-6-hydroxy-1,2,3,4,5,6-hexahydro-2,4-dioxopyrimidine 5-carboxylate as a yellow vitreous solid. The identity of this compound is established by nuclear magnetic resonance spectrum. The product gives a single spot on the silica gel thin-layer plate (chloroform-methanol=6:1 V/V).

EXAMPLE 3

In a pressure-resistant glass tubular reactor of 50 ml. capacity, 510 mg. (3.0 mmoles) of methyl 1,2,3,4-tetrahydro-2,4-dioxopyrimidine-5-carboxylate is suspended in 20 ml. of water and the suspension is frozen in a dry ice-ethanol bath. Following addition of 20 ml. of trifluoroacetic acid, about 290 mg. of trifluoromethylhypofluorite is dissolved. After closing the reactor tightly, the reaction mixture is allowed to return spontaneously to room temperature. With the increasing temperature, the reaction proceeds swiftly to yield a homogeneous solution. This reaction mixture is stirred overnight. Nitrogen gas is bubbled through the mixture to remove the excess trifluoromethylhypofluorite, followed by addition of sodium bicarbonate (540 mg.). The solvent is distilled off under reduced pressure, whereupon a colorless syrupy product is obtained. Following addition of 30 ml. of acetone, the insolubles are filtered off and the acetone solution is concentrated under reduced pressure to recover 1.15 g. of a pale yellow syrup. By silica gel TLC and NMR, this product is identified as methyl 5-fluoro-6-hydroxy-1,2,3,4,5,6-hexahydro-2,4-dioxopyrimidine-5-carboxylate.

EXAMPLE 4

In a pressure-resistant glass tubular reactor of 300 ml. capacity, 25 ml. of methanol is mixed with 50 ml. of fluorotrichloromethane and the mixture is sufficiently cooled in a dry-ice ethanol bath. In this mixture is dissolved about 1.1 g. of trifluoromethylhypofluorite and, then, 1.36 g. (8.0 mmoles) of methyl 1,2,3,4-tetrahydro-2,4-dioxopyrimidine-5-carboxylate is suspended, followed by addition of 80 ml. of the methanol previously cooled sufficiently in a dry ice-ethanol bath. After the reactor is tightly closed, the reaction mixture is allowed to return spontaneously to room temperature, with constant stirring. With the increasing temperature, the starting material reacts swiftly to yield a homogeneous solution. The solution is stirred overnight, after which nitrogen gas is bubbled through the solution to remove the excess trifluoromethylhypofluorite. The solvent is then distilled off, whereupon a white solid is obtained. This solid is purified by chromatography on a column of silica gel (solvent:chloroform containing 1 to 10 V/V% of methanol) to give 1.52 g. of methyl 5-fluoro-6-methoxy-1,2,3,4,5,6-hexahydro-2,4-dioxopyrimidine-5-carboxylate as well as 0.31 g. of the unreacted starting material. Recrystallization of this product from acetone and hexane yields 1.26 g. of colorless flakes.

Melting point: 165°–166° C.

NMR spectrum (DMSO-d$_6$) δ: 3.38(3H,s), 3.85(3H,s), 4.77(1H,d×d, $J_{HF}$=2H$_Z$, J=5H$_Z$; after addition of deuterium oxide, d, $J_{HF}$=2H$_Z$), 8.77(1H, broad), 10.92(1H, broad)

Elemental analysis, for C$_7$H$_9$FN$_2$O$_5$: Calcd.: C, 38.19; H, 4.12; N, 12.76; F, 8.63. Found: C, 38.49; H, 4.06; N, 12.50; F, 7.92.

EXAMPLE 5

In 200 ml. of water is suspended 920 mg. of ethyl 1,2,3,4-tetrahydro-2,4-dioxopyrimidine-5-carboxylate and, while the suspension is stirred vigorously at room temperature, a gaseous mixture of fluorine (25 V/V%) and nitrogen is introduced. In the course, the starting material dissolves to yield a homogeneous solution. When 2.6 mole equivalents of said gaseous mixture has been introduced, the ultraviolet absorption spectrum of the reaction mixture is measured. When the absence of unreacted starting compounds is confirmed by the spectrum, the reaction is stopped. Following addition of 1.10 g. of calcium carbonate, the reaction mixture is stirred for a while, after which the insolubles are filtered off. The filtrate is concentrated to dryness under reduced pressure, whereupon a white solid is obtained. This product is suspended in 50 ml. of acetone and the insolubles are filtered off. The acetone-solubles are subjected to column chromatography on silica gel (solvent: chloroform containing 1.5 V/V% of methanol), followed by concentration of the fraction containing the desired compound under reduced pressure to recover a white solid product. Recrystallization from methanol-chloroformhexane yields 561 mg. of colorless prisms of ethyl 5-fluoro-6-hydroxy-1,2,3,4,5,6-hexahydro-2,4-dioxopyrimidine-5-carboxylate. melting point: 163°–165° C.

NMR spectrum (DMSO-d$_6$) δ: 1.22(3H,t, J=7H$_Z$), 4.28(2H, q, J=7H$_Z$), 4.93(1H, d×d, $J_{HF}$=3H$_Z$, J=5H$_Z$; after addition of deuterium oxide, d, $J_{HF}$=3H$_Z$), 6.3(1H, broad), 8.48(1H, broad), 10.80(1H, broad).

Elemental analysis, for C$_7$H$_9$FN$_2$O$_5$: Calcd.: C, 38.19; H, 4.12; N, 12.73. Found: C, 37.90; H, 3.94; N, 12.87.

EXAMPLE 6

In 200 ml. of water is suspended 1.54 g. of isopropyl 1,2,3,4-tetrahydro-2,4-dioxopyrimidine-5-carboxylate and 3 mole equivalents of a gaseous mixture of fluorine gas (25 V/V%) and nitrogen is introduced into the suspension to effect fluorination. The reaction mixture is worked up by a procedure similar to that described in Example 1 and the product is purified by column chromatography on silica gel. The fraction is concentrated under reduced pressure to recover 1.44 g. of a white solid. Recrystallization from acetone and hexane yields 1.06 g. of isopropyl 5-fluoro-6-hydroxy-1,2,3,4,5,6-hexahydro-2,4-dioxopyrimidine-5-carboxylate as colorless needles.

Melting Point: 179°–181° C.

NMR spectrum (DMSO-d$_6$) δ: 1.22(6H, d, J=6H$_Z$), 4.92(1H, m; after addition of deuterium oxide, d, $J_{HF}$=3H$_Z$), 5.02(1H, m), 7.07(1H, d, J=5H$_Z$), 8.52(1H, broad), 10.82(1H, broad).

Elemental analysis, for C$_8$H$_{11}$FN$_2$O$_5$: Calcd.: C, 41.03; H, 4.74; N, 11.96. Found: C, 41.08; H, 4.52; N, 11.60.

EXAMPLE 7

In 150 ml. of water is suspended 3.18 g. of n-butyl 1,2,3,4-tetrahydro-2,4-dioxopyrimidine-5-carboxylate and, under vigorous stirring, a gaseous mixture of fluorine gas (25 V/V %) and nitrogen is introduced. During this procedure the starting material dissolves to yield a homogeneous solution. When 4 mole equivalents of said gaseous mixture has been introduced, the reaction mixture is worked up by a procedure similar to that described in Example 1 to recover a white solid. This product is combined with a white solid obtained by fluorination of 2.12 g. of the same starting material and, then, purified by chromatography on silica gel. The desired fraction is concentrated under reduced pressure to recover 4.63 g. of a white solid. Recrystallization of the solid from acetone and chloroform yields 3.08 g. of n-butyl 5-fluoro-6-hydroxy-1,2,3,4,5,6-hexahydro-2,4-dioxopyrimidine-5-carboxylate as colorless flakes.

Melting Point: 162°–163° C.

NMR spectrum (DMSO-$d_6$) δ: 0.90(3H, m), 1.1–1.9(4H, m), 4.22(2H, t, J=6$H_Z$), 4.90(1H, m; after addition of deuterium oxide, d, $J_{HF}$=3$H_Z$), 7.07(1H, d, J=5$H_Z$), 8.53(1H, broad), 10.87(1H, broad).

Elemental analysis, for $C_9H_{13}FN_2O_5$: Calcd.: C, 43.55; H, 5.28; N, 11.29. Found: C, 43.26; H, 5.16; N, 11.46.

EXAMPLE 8

In 300 ml. of water is suspended 4.24 g. of sec-butyl 1,2,3,4-tetrahydro-2,4-dioxopyrimidine-5-carboxylate and, while the suspension is vigorously stirred, fluorine gas previously diluted with 3.3 times its volume of nitrogen is introduced with the reaction temperature being maintained at 24°–28° C. A total of 1.8 mole equivalents of fluorine based on the substrate is introduced, whereby a colorless clear solution is obtained. Following the addition of 2.5 g. of sodium hydrogen sulfite and, then, of 7.5 g. of calcium carbonate, the reaction mixture is filtered and the filtrate is concentrated to dryness under reduced pressure. Following addition of 300 ml. of acetone and thorough stirring, the mixture is filtered and the filtrate is concentrated to dryness under reduced pressure to give 4.59 g. of a white powder. A 1.59 g. portion of the powder is taken and chromatographed on a column of silica gel (solvent:benzene-acetone-=2:1 V/V) to recover a white crystalline solid of sec-butyl 5-fluoro-6-hydroxy-1,2,3,4,5,6-hexahydro-2,4-dioxopyrimidine-5-carboxylate.

Melting Point: 183°–184° C.(decomp.).

NMR spectrum (DMSO-$d_6$) δ: 0.86(3H, t, J=7$H_Z$), 1.21(3H, d, J=7$H_Z$), 1.59(2H, m, J=7$H_Z$), 4.7–5.1(2H, m), 7.16(1H, broad), 8.60(1H, broad), 10.89(1H, broad).

Elemental analysis, for $C_9H_{13}FN_2O_5$: Calcd.: C, 43.55; H, 5.28; N, 11.29. Found: C, 43.40; H, 5.26; N, 11.19.

EXAMPLE 9

In 200 ml. of water is suspended 1.77 g. of 2-chloroethyl 1,2,3,4-tetrahydro-2,4-dioxopyrimidine-5-carboxylate and, while the suspension is stirred vigorously, a gaseous mixture of fluorine (25 V/V %) and nitrogen is introduced. When 4.2 molar equivalents of the gaseous mixture has been introduced, the consumption of the starting material is confirmed by ultraviolet absorption spectrum and the reaction product is isolated by a procedure similar to that described in Example 1. The product is purified by chromatography on a column of silica gel and, then, recrystallized from acetone-chloroform-hexane to give 370 mg. of 2-chloroethyl 5-fluoro-6-hydroxy-1,2,3,4,5,6-hexahydro-2,4-dioxopyrimidine-5-carboxylate as colorless prisms.

Melting Point: 180°–182° C.

NMR spectrum (DMSO-$d_6$) δ: 3.83(2H, m), 4.52(2H, m), 4.97(1H, m; after addition of deuterium oxide, d, $J_{HF}$=3$H_Z$), 7.17(1H, d, J=5$H_Z$), 8.53(1H, broad), 10.90(1H, broad).

Elemental analysis, for $C_7H_8ClFN_2O_5$: Calcd.: C, 33.02; H, 3.17; N, 11.01. Found: C, 33.44; H, 3.05; N, 11.11.

EXAMPLE 10

In 200 ml. of water is suspended 1.84 g. of methyl 3-methyl-1,2,3,4-tetrahydro-2,4-dioxopyrimidine-5-carboxylate and, under vigorous stirring, 3 molar equivalents of a gaseous mixture of fluorine (25 V/V %) and nitrogen is introduced. After this fluorination, the reaction mixture is worked up by a procedure similar to that described in Example 1 and the resultant yellow solid is purified by chromatography on a column of silica gel. The resultant fractions yield 1.27 g. of a white solid. On recrystallization from acetone-chloroform-hexane, there is obtained methyl 5-fluoro-6-hydroxy-3-methyl-1,2,3,4,5,6-hexahydro-2,4-dioxopyrimidine-5-carboxylate as colorless flakes.

Melting Point: 160°–161° C.

NMR spectrum (DMSO-$d_6$) δ: 3.07(3H, s), 3.80(3H, s), 4.95(1H, m; after addition of deuterium oxide, d, $J_{HF}$=3$H_Z$), 7.17(1H, d, J=5$H_Z$), 8.85(1H, broad).

Elemental analysis, for $C_7H_9FN_2O_5$: Calcd.: C, 38.19; H, 4.12; N, 12.73. Found: C, 38.33; H, 4.04; N, 12.84.

EXAMPLE 11

In a 500 ml.-glass reactor fitted with a Teflon ® stirrer blade, a Teflon ® gas inlet, a thermometer, and a gas outlet connected to a fluorine gas trap, 980 mg. of methyl 1-(2-tetrahydrofuryl)-1,2,3,4-tetrahydro-2,4-dioxopyrimidine-5-carboxylate is suspended in 200 ml. of water, and a gaseous mixture of fluorine gas (25 V/V %) and nitrogen is introduced at room temperature. In the course of this treatment, the starting material dissolves to yield a homogeneous solution. When 4 molar equivalents of the gaseous mixture has been introduced, the ultraviolet absorption spectrum of the reaction mixture is determined to confirm the absence of starting compound. The reaction is then terminated and 2.0 g. of calcium carbonate is added to the reaction mixture to neutralize the hydrogen fluoride. Then, following addition of 20 ml. of a 1 M aqueous solution of sodium hydrogen sulfite, the resultant precipitate is filtered off and the filtrate is concentrated to dryness under reduced pressure to give a white solid mass. This product is suspended in 50 ml. of acetone and the insolubles are filtered off. The acetone-solubles are chromatographed on a column of silica gel (solvent: chloroform including 1 V/V % of methanol) and the fractions containing the desired compound are concentrated under reduced pressure to recover a white solid. Recrystallization from acetone-chloroform-hexane yields 485 mg. of methyl 5-fluoro-1-(2-tetrahydrofuryl)-6-hydroxy-1,2,3,4,5,6-hexahydro-2,4-dioxopyrimidine-5-carboxylate as colorless flakes.

Melting Point: 165°–170° C.

NMR spectrum (DMSO-$d_6$) δ: 1.7–2.2(4H, m), 3.75 and 3.82(5H), 5.0–5.2(1H, m; after addition of deuterium oxide, d, $J_{HF}$=3.5$H_Z$), 5.73(1H, m), 7.28 and 7.33(1H, disappears upon addition of deuterium oxide), 11.08(1H, broad).

Elemental analysis, for $C_{10}H_{13}FN_2O_6$: Calcd.: C, 43.48; H, 4.74; N, 10.14. Found: C, 43.45; H, 4.63; N, 10.02.

EXAMPLE 12

In 200 ml. of glacial acetic acid is suspended 850 mg. of methyl 1,2,3,4-tetrahydro-2,4-dioxopyrimidine-5-carboxylate and, under vigorous stirring, a gaseous mixture of fluorine (10 V/V %) and nitrogen is introduced with the reaction temperature being maintained at 18.0°–19.0° C. In the course of this reaction, the starting material dissolves to yield a homogeneous solution. This reaction mixture is concentrated to dryness under reduced pressure to recover a pale yellow vitreous solid.

This product is subjected to column chromatography on silica gel (solvent:benzene-acetone=4:1 (V/V)) and the fractions rich in the desired compound are concentrated under reduced pressure to give 1.00 g. of methyl 6-acetoxy-5-fluoro-1,2,3,4,5,6-hexahydro-2,4-dioxopyrimidine-5-carboxylate as colorless neeldes.

NMR spectrum (DMSO-$d_6$) δ: 2.08(3H, s), 3.83(3H, s), 6.23(1H, dxd, $J_{HF}$=2H$_Z$, J=6H$_Z$; after addition of deuterium oxide, d, $J_{HF}$=2H$_Z$), 9.10(1H, broad), 11.33(1H, broad)

EXAMPLE 13

A gaseous mixture of fluorine (10 V/V %) and nitrogen containing 2.1 molar equivalents of fluorine is introduced into a suspension of 1.07 g. of n-octyl 1,2,3,4-tetrahydro-2,4-dioxopyrimidine-5-carboxylate in 200 ml. of acetic acid, at 20°–25° C. over a period of 4 hours. The resultant colorless clear mixture is concentrated to dryness under reduced pressure to give 1.44 g. of crude n-octyl 5-fluoro-6-acetoxy-1,2,3,4,5,6-hexahydropyrimidine-5-carboxylate as a white solid.

NMR spectrum (DMSO-$d_6$) δ: 0.67–1.83(15H, m), 2.08(3H, s), 4.28(2H, m), 6.19(1H, dxd, J 5.5,2H$_Z$; after addition of deuterium oxide, d, J=2H$_Z$), 9.1, 11.3(each 1H, broad)

EXAMPLE 14

A gaseous mixture of fluorine (15 V/V %) and nitrogen containing 5 molar equivalents of fluorine is introduced into a suspension of 2.04 g. of stearyl 1,2,3,4-tetrahydro-2,4-dioxopyrimidine-5-carboxylate in 200 ml. of acetic acid, at 24° C. over a period of 8.5 hours. The insolubles are filtered off to recover 89% of unreacted starting material and the filtrate is concentrated under reduced pressure. The residue is dissolved in 10 ml. of ethanol and heated under reflux overnight. The solvent is distilled off and the residue is chromatographed on silica gel (solvent:chloroform-ethyl acetate=1.1 (V/V)) to recover 54 mg of stearyl 5-fluoro-6-ethoxy-1,2,3,4,5,6-hexahydro-2,4-dioxopyrimidine-5-carboxylate.

Melting Point: 104°–106° C.(recrystallized from chloroform-hexane).

NMR spectrum (DMSO-$d_6$) δ: 0.6–1.8(38H, m), 3.3–3.93(2H, m), 2.93–4.42(2H, m), 4.82(1H, m; after addition of deuterium oxide, d, J=2H$_Z$), 8.70, 10.83(each 1H, broad).

Elemental analysis, for $C_{25}H_{45}FN_2O_5 \cdot 1/2H_2O$: Calcd.: C, 62.34; H, 9.62; N, 5.82. Found: C, 62.52; H, 9.45; N, 5.85.

EXAMPLE 15

In 200 ml. of water is suspended 1.55 g. of 1,2,3,4-tetrahydro-2,4-dioxopyrimidine-5-carboxamide, and fluorine gas previously diluted with 3 times its volume of nitrogen is bubbled through the suspension. With the reaction temperature maintained at 27°–30° C., about 5 molar equivalents of fluorine based on the substrate is introduced (over about 4 hours) and after removal of the unreacted starting material by filtration, 2.5 g. of sodium hydrogen sulfite and 9.0 g. of calcium carbonate are added. After thorough stirring, the reaction mixture is filtered and the filtrate is concentrated under reduced pressure. The concentrate is dissolved in 200 ml. of acetone. The solution is concentrated to dryness and the resultant solid is recrystallized from a solvent mixture of acetone and chloroform to give 0.74 g. of 5-fluoro-6-hydroxy-1,2,3,4,5,6-hexahydro-2,4-dioxopyrimidine-5-carboxamide as a crystalline powder.

Melting Point: 188°–189° C. (decomp.).

NMR spectrum (DMSO-$d_6$) δ: 4.86(1H, m), 6.82(1H, d, J=5H$_Z$), 7.75(1H, broad), 7.93(1H, broad), 8.48(1H, broad), 10.63(1H, broad).

Elemental analysis, for $C_5H_6FN_3O_4$: Calcd.: C, 31.42; H, 3.16; N, 21.99. Found: C, 31.25; H, 3.21; N, 22.09.

EXAMPLE 16

While a suspension of 1.69 g. of 1,2,3,4-tetrahydro-2,4-dioxopyrimidine-5-(N-methyl)-carboxamide in 200 ml. of water is vigorously stirred, fluorine gas previously diluted with 3 times its volume of nitrogen is introduced with the reaction temperature maintained at 25°–27° C. When about 3.5 molar equivalents of fluorine has been introduced per mole of the substrate (over about 3.5 hours), the reaction mixture becomes colorless and clear. At this time it is neutralized with calcium carbonate (4.3 g.) and filtered. The filtrate is concentrated to dryness and the concentrate is dissolved in methanol. The solution is concentrated to dryness and chromatographed on a column of silica gel (solvent: benzene-acetone=1:1–1:5) to give 0.73 g. of 5-fluoro-6-hydroxy-1,2,3,4,5,6-hexahydro-2,4-dioxopyrimidine-5-(N-methyl)-carboxamide as a white powder.

Melting Point: 193°–194° C.(decomp.).

NMR spectrum (DMSO-$d_6$) δ: 2.63(3H, d, J=5H$_Z$; ater addition of deuterium oxide, s), 4.86(1H, m; after addition of deuterium oxide, d, J=2H$_Z$), 6.84(1H, broad), 8.40(2H, broad), 10.61(1H, broad).

Elemental analysis, for $C_6H_8FN_3O_4$: Calcd.: C, 35.13; H, 3.93; N, 20.48. Found: C, 34.92; H, 3.98; N, 20.51.

EXAMPLE 17

In 50 ml. of water is dissolved 1.06 g. of 1,2,3,4-tetrahydro-2,4-dioxopyrimidine-5-(N,N-diethyl)-carboxamide, and under vigorous stirring, fluorine gas previously diluted with 3 times its volume of nitrogen is introduced (reaction temp. 27°–29° C.). When 5 molar equivalents of fluorine has been introduced per mole of the substrate (over about 2.5 hours), the reaction mixture is directly concentrated to dryness and the concentrate is chromatographed on a column of silica gel (solvent:benzene-acetone=2:1) to give 0.17 g. of 5-fluoro-6-hydroxy-1,2,3,4,5,6-hexahydro-2,4-dioxopyrimidine-5-(N,N-diethyl)-carboxamide.

NMR spectrum (DMSO-$d_6$) δ: 0.85–1.33(6H, m), 3.05–3.70(4H, m), 4.99(1H, broad d, J=5H$_Z$; after addition of deuterium oxide, s (broad)), 6.6–7.4(1H, broad), 8.37(1H, broad), 10.7(1H, broad).

EXAMPLE 18

Fluorine gas previously diluted with 3 times its volume of nitrogen is bubbled into a mixture of 1.57 g. of N-(1,2,3,4-tetrahydro-2,4-dioxopyrimidine-5-carbonyl)-morpholine and 150 ml. of water with constant stirring and the reaction temperature maintained at 15°–23° C. When about 3 molar equivalents of fluorine has been introduced per mole of the substrate (over about 2.5 hours), 1.0 g. of sodium hydrogen sulfite and 5.0 g. of calcium carbonate are added. The mixture is filtered and the filtrate is concentrated. The residue is dissolved in acetone and chromatographed on silica gel (solvent:-benzene-acetone=1:1) to give 0.33 g. of N-(5-fluoro-6-hydroxy-1,2,3,4,5,6-hexahydro-2,4-dioxopyrimidine-5-carbonyl)morpholine as a white powder.

Melting Point: 183°–184° C.(decomp.).

NMR spectrum (DMSO-$d_6$) δ: 3.60(8H, s), 5.03(1H, t, J=5H$_Z$), 6.92(1H, d, J=5H$_Z$), 8.40(1H, broad), 10.77(1H, broad).

Elemental analysis, for $C_9H_{12}FN_3O_5$: Calcd.: C, 41.38; H, 4.63; N, 16.09. Found: C, 41.20; H, 4.54; N, 16.23.

EXAMPLE 19

In 200 ml. of acetic acid is dissolved 1.06 g. of 1,2,3,4-tetrahydro-2,4-dioxopyrimidine-5-(N-tert-butyl)carboxamide and under vigorous stirring, fluorine gas previously diluted with 9 times its volume of nitrogen gas is introduced. When 2 molar equivalents of fluorine has been introduced per mole of the substrate (over about 2 hours), the reaction mixture is concentrated to dryness. The residue is dissolved in a small amount of acetone, followed by addition of benzene. The resultant precipitate is recovered by filtration to give 0.94 g. of 5-fluoro-6-acetoxy-1,2,3,4,5,6-hexahydro-2,4-dioxopyrimidine- as a white powder.

Melting Point: 191°–193° C.(decomp.).

NMR spectrum (DMSO-$d_6$) δ: 1.29(9H, s), 2.10(3H, s), 6.14(1H, broad d, J=6H$_Z$), 8.19(1H, broad s), 9.09(1H, broad), 11.01(1H, broad).

Elemental analysis, for $C_{11}H_{16}FN_3O_4$: Calcd.: C, 45.68; H, 5.58; N, 14.53. Found: C, 44.92; H, 5.36; N, 14.89.

EXAMPLE 20

In a pressure-resistant glass tubular reactor of 100 ml. capacity, 1.10 g. (8.0 mmoles) of 1,2,3,4-tetrahydro-2,4-dioxopyrimidine-5-carbonitrile is suspended in 35 ml. of water and the suspension is frozen in a dry ice-ethanol bath. To this is added 35 ml. of fluorotrichloromethane and in the above cooling bath, trifluoromethylhypofluorite (about 1.2 g.) is dissolved in the mixture. After the reactor is hermetically sealed, the reaction mixture is stirred at room temperature for 40 hours, whereby the starting compound in completely reacted and dissolved. The excess trifluoromethylhypofluorite is removed by the passage of nitrogen gas and following addition of sodium bicarbonate (690 mg.), the solvent is removed under reduced pressure. By the above procedure is obtained 1.74 g. of a brown-colored vitreous solid. Two distinct spots are shown on the silica gel thin-layer chromatogram. By nuclear magnetic resonance spectrum, it is identified as a mixture (approximately 1:1) of 5-fluoro-6-hydroxy-1,2,3,4,5,6-hexahydro-2,4-dioxopyrimidine-5-carbonitrile and $N^3$,5-difluoro-6-hydroxy-1,2,3,4,5,6-hexahydro-2,4-dioxopyrimidine-5-carbonitrile.

NMR spectrum (DMSO-$d_6$) δ: 5.33(1H, m; after addition of deuterium oxide, d, $J_{HF}$=3H$_Z$ 7.7–8.2(1H, broad), 9.00(1H, broad), 10.3–11.0(½H, broad, assignable to $N^3$-H)

EXAMPLE 21

In 150 ml. of water is suspended 2.05 g. of 1,2,3,4-tetrahydro-2,4-dioxopyrimidine-5-carbonitrile and, with vigorous stirring, fluorine gas previously diluted with 3 times its volume of nitrogen gas is introduced (reaction mixture 26°–29° C.). When about 4.5 molar equivalents of fluorine has been introduced (over about 5 hours), the reaction mixture is concentrated to dryness and the residue is chromatographed on a column of silica gel (solvent:chloroform-methanol=13:1) to give 1.86 g. of 5-fluoro-6-hydroxy-1,2,3,4,5,6-hexahydro-2,4-dioxopyrimidine-5-carbonitrile as a white crystalline powder.

Melting Point: 158°–160° C.(decomp.).

NMR spectrum (DMSO-$d_6$) δ: 5.35(1H, m), 7.75(1H, broad), 9.00(1H, broad), 11.40(1H, broad).

Elemental analysis, for $C_5H_4FN_3O_3$: Calcd.: C, 34.69; H, 2.33; N, 24.27. Found: C, 34.39; H, 2.27; N, 24.16.

EXAMPLE 22

In 200 ml. of absolute methanol is dissolved 8.0 g. (38.8 mmoles) of methyl 5-fluoro-6-hydroxy-1,2,3,4,5,6-hexahydro-2,4-dioxopyrimidine-5-carboxylate, and under ice-cooling, dry hydrogen chloride gas is introduced until about 14 g. of hydrogen chloride is absorbed. The reaction mixture is allowed to stand at about 5° C. overnight and, then, concentrated to dryness under reduced pressure. The resultant solid is chromatographed on a column of silica gel (solvent:acetone-chloroform=1:4 (V/V)) to obtain 7.64 g. of colorless crystals.

Based on its thin-layer chromatographic mobility and IR and NMR spectra, this product is found to be identical with an authentic sample of methyl 5-fluoro-6-methoxy-1,2,3,4,5,6-hexahydro-2,4-dioxopyrimidine-5-carboxylate.

EXAMPLE 23

In 30 ml. of dry dioxane is dissolved 1.03 g. of methyl 5-fluoro-6-hydroxy-1,2,3,4,5,6-hexahydro-2,4-dioxopyrimidine-5-carboxylate, followed by addition of 1.0 g. of cyclohexanol. Then, a sufficient amount of hydrogen chloride is introduced and the reaction mixture is heated under reflux for 2 hours. The reaction mixture is concentrated to dryness, and a mixture of benzene-n-hexane is added to the concentrate. The resultant precipitate is recovered by filtration and chromatographed on a column of silica gel (solvent:benzene-acetone=3:1 V/V) to give 0.71 g. of methyl 5-fluoro-6-cyclohexyloxy-1,2,3,4,5,6-hexahydro-2,4-dioxopyrimidine-5-carboxylate.

Melting Point: 196°–197° C.

NMR spectrum (DMSO-$d_6$) δ: 0.9–2.0(10H, broad m), 3.60(1H, m), 3.83(3H, s), 4.97(1H, d×d J=5H$_Z$, J=2H$_Z$), 8.8(1H, broad), 11.00(1H, broad).

Elemental analysis, for $C_{12}H_{17}FN_2O_5$: Calcd.: C, 50.00; H, 5.94; N, 9.72. Found: C, 49.94; H, 5.83; N, 9.78.

EXAMPLE 24

In 10 ml. of dry dioxane is dissolved 0.52 g. of methyl 5-fluoro-6-hydroxy-1,2,3,4,5,6-hexahydro-2,4-dioxopyrimidine-5-carboxylate, followed by the addition of 0.65 g. of n-octyl alcohol, 15 mg. of p-toluenesulfonic acid and 0.5 g. of anhydrous magnesium sulfate. The mixture is heated under stirring and reflux for 4 hours. The reaction mixture is filtered and concentrated.

To the residue is added benzene, and then hexane and the resultant precipitate is recovered by filtration. The filtrate is chromatographed on a column of silica gel (solvent:benzene-acetone=3:1) to give 0.65 g. of methyl 5-fluoro-6-n-octyloxy-1,2,3,4,5,6-hexahydro-2,4-dioxopyrimidine-5-carboxylate as a white powder.

Melting Point: 147°–148° C.

NMR spectrum (DMSO-$d_6$) δ: 0.9(3H, broad), 1.3(12H, broad s), 3.6(2H, broad), 3.82(3H, s), 4.82(1H, d×d, J=5H$_Z$, J=2H$_Z$), 8.9(1H, broad), 11.0(1H, broad).

Elemental analysis, for $C_{14}H_{23}FN_2O_5$: Calcd.: C, 52.82; H, 7.28; N, 8.80. Found: C, 52.84; H, 7.27; N, 8.71.

EXAMPLE 25

In 100 ml. of dry methanol is dissolved 2.20 g. (10 mmoles) of ethyl 5-fluoro-6-hydroxy-1,2,3,4,5,6-hexahydro-2,4-dioxopyrimidine-5-carboxylate and, under ice-cooling, dry hydrogen chloride (about 10 g.) is introduced into the solution. The solution is allowed to stand at about 5° C. for 2 days, after which time it is concentrated to dryness under reduced pressure. To the resultant solid is added 100 ml. of dry methanol and an excess of dry hydrogen chloride is introduced as above. The reaction mixture is allowed to stand at room temperature overnight and then concentrated to dryness under reduced pressure. The residue is chromatographed on a column of silica gel to give 2.0 g. of methyl 5-fluoro-6-methoxy-1,2,3,4,5,6-hexahydro-2,4-dioxopyrimidine-5-carboxylate.

EXAMPLE 26

In 50 ml. of dry n-butanol is suspended 1.03 g. (5 mmoles) of methyl 5-fluoro-6-hydroxy-1,2,3,4,5,6-hexahydro-2,4-dioxopyrimidine-5-carboxylate and, at room temperature, dry hydrogen chloride is bubbled through the suspension until the reaction temperature has reached about 70° C. The reaction mixture is allowed to stand at room temperature overnight, after which it is concentrated to dryness under reduced pressure. To the residue is added 50 ml. of dry n-butanol and, after the passage of dry hydrogen chloride in the same manner as above, the solution is concentrated to dryness under reduced pressure. To the residue is added 30 ml. of n-hexane and the precipitates are recovered by filtration to give 1.40 g. of colorless solid. This product is chromatographed on a column of silica gel (solvent:acetone-chloroform=1:5 (V/V)) to recover 1.25 g. of n-butyl 5-fluoro-6-n-butoxy-1,2,3,4,5,6-hexahydro-2,4-dioxopyrimidine-5-carboxylate.

Melting Point: 138°–139° C.(recrystallized from chloroform-n-hexane).

NMR spectrum (DMSO-$d_6$) δ: 0.66–1.10(6H, broad), 1.00–1.85(8H, broad), 3.30–3.80(2H, m), 4.24(2H, t, J=6H$_Z$), 4.74(1H, m), 8.77(1H, broad), 10.90(1H, broad).

Elemental analysis, for $C_{13}H_{21}FN_2O_5$: Calcd.: C, 51.31; H, 6.96; N, 9.21. Found: C, 51.39; H, 6.94; N, 9.36.

EXAMPLE 27

In 200 ml. of dry ethanol is dissolved 5.0 g. (22.75 mmoles) of ethyl 5-fluoro-6-hydroxy-1,2,3,4,5,6-hexahydro-2,4-dioxopyrimidine-5-carboxylate and, under ice-cooling, about 10 g. of dry hydrogen chloride is introduced. The solution is allowed to stand at room temperature overnight and, then, concentrated to dryness under reduced pressure. The residue is subjected to column chromatography on silica gel (solvent:acetone-chloroform=1:4 V/V)) to recover 5.30 g. of ethyl 5-fluoro-6-ethoxy-1,2,3,4,5,6-hexahydro-2,4-dioxopyrimidine-5-carboxylate.

Melting Point: 179°–181° C.(Recrystallized from acetone-chloroform-n-hexane).

NMR spectrum (DMSO-$d_6$) δ: 0.96–1.50(6H, m), 3.20–3.97(2H, m), 4.30(2H, q, J=7H$_Z$), 4.80(1H, d×d), 8.77(1H, broad), 10.90(1H, broad).

Elemental analysis, for $C_9H_{13}FN_2O_5$: Calcd.: C, 43.55; H, 5.28; N, 11.29. Found: C, 43.37; H, 5.21; N, 11.13.

EXAMPLE 28

In 100 ml. of dry ethanol is dissolved 4.12 g. (20 mmoles) of methyl 5-fluoro-6-hydroxy-1,2,3,4,5,6-hexahydro-2,4-dioxopyrimidine-5-carboxylate, and after about 12 g. of dry hydrogen chloride has been introduced, the solution is heated at 70° C. for 30 minutes. The reaction mixture is concentrated to dryness under reduced pressure and, after the addition of 100 ml. of dry ethanol to the residue, about 10 g. of dry hydrogen chloride is introduced again. The mixture is allowed to stand at room temperature overnight. It is then concentrated to dryness under reduced pressure and the residue is purified by column chromatography on silica gel as in Example 27 to give 3.61 g. of ethyl 5-fluoro-6-ethoxy-1,2,3,4,5,6-hexahydro-2,4-dioxopyrimidine-5-carboxylate.

EXAMPLE 29

In 20 ml. of dimethoxyethane is dissolved 3.30 g. (15 mmoles) of ethyl 5-fluoro-6-hydroxy-1,2,3,4,5,6-hexahydro-2,4-dioxopyrimidine-5-carboxylate together with 1.74 g. (30 mmoles) of allyl alcohol and a catalytic amount of methanesulfonic acid. The solution is heated under reflux for 1 hour, after which it is concentrated under reduced pressure. The residue is purified by a procedure similar to that described in Example 27 to recover 2.40 g. of ethyl 5-fluoro-6-allyloxy-1,2,3,4,5,6-hexahydro-2,4-dioxopyrimidine-5-carboxylate.

Melting Point: 153°–154° C.(Recrystallized from acetone-chloroform-n-hexane).

NMR spectrum (DMSO-$d_6$) δ: 1.20(3H, t, J=7H$_Z$), 3.94–4.57(4H, m), 4.82(1H, d×d), 4.90–6.25(3H, m), 8.92(1H, broad), 11.03(1H, broad).

Elemental analysis, for $C_{10}H_{13}FN_2O_5$: Calcd.: C, 46.16; H, 5.04; N, 10.76. Found: C, 45.91; H, 4.99; N, 10.61.

EXAMPLE 30

A solution of 3.30 g. (15 mmoles) of ethyl 5-fluoro-6-hydroxy-1,2,3,4,5,6-hexahydro-2,4-dioxopyrimidine-5-carboxylate, 1.01 g. (18 mmoles) of propargyl alcohol, a catalytic amount of methanesulfonic acid and 20 ml. of dimethoxyethane is heated under reflux for 1 hour. The reaction mixture is purified as in Example 27 to give 1.935 g. of ethyl 5-fluoro-6-propargyloxy-1,2,3,4,5,6-hexahydro-2,4-dioxopyrimidine-5-carboxylate.

Melting Point: 151°–152° C.(Recrystallized from acetone-chloroform-n-hexane).

NMR spectrum (DMSO-$d_6$) δ: 1.17(3H, t, J=7H$_Z$), 3.34(1H, broad s), 4.0–4.6(4H, m), 5.00(1H, d×d), 8.91(1H, broad), 11.07(1H, broad).

Elemental analysis, for $C_{10}H_{11}FN_2O_5 \cdot \frac{1}{4}H_2O$: Calcd.: C, 45.96; H, 4.43; N, 10.84. Found: C, 45.97; H, 4.24; N, 10.80.

EXAMPLE 31

A solution comprising 4.40 g. (20 mmoles) of ethyl 5-fluoro-6-hydroxy-1,2,3,4,5,6-hexahydro-2,4-dioxopyrimidine-5-carboxylate, 4.44 g. (60 mmoles) of tert-butanol, 300 mg. of methanesulfonic acid and 30 ml. of dimethoxyethane is heated under reflux for 1.5 hours. The reaction mixture is concentrated under reduced pressure and the residue is purified by a procedure similar to that described in Example 27 to give 1.50 g. of ethyl 5-fluoro-6-tert-butyloxy-1,2,3,4,5,6-hexahydro-2,4-dioxopyrimidine-5-carboxylate.

Melting Point: 231°–232° C.(Recrystallized from acetone-chloroform-n-hexane).

NMR spectrum (DMSO-$d_6$) δ: 1.14(9H, s), 1.16(3H, t, $J=7H_Z$), 4.33(3H, t, $J=7H_Z$), 4.97(1H, d×d), 8.57(1H, broad), 10.82(1H, broad).

Elemental analysis, for $C_{11}H_{17}FN_2O_5 \cdot \frac{1}{4}H_2O$: Calcd.: C, 47.06; H, 6.10; N, 9.98. Found: C, 47.17; H, 5.79; N, 10.30.

EXAMPLE 32

A solution comprising 3.30 g. (15 mmoles) of ethyl 5-fluoro-6-hydroxy-1,2,3,4,5,6-hexahydro-2,4-dioxopyrimidine-5-carboxylate, 4.06 g. (15 mmoles) of stearyl alcohol, a catalytic amount of methanesulfonic acid and 30 ml. of dimethoxyethane is heated under reflux for 1.5 hours. The reaction mixture is concentrated under reduced pressure and the residue is purified by a procedure similar to that described in Example 27 to give 4.55 g. of ethyl 5-fluoro-6-n-octadecyloxy-1,2,3,4,5,6-hexahydro-2,4-dioxopyrimidine-5-carboxylate.

Melting Point: 114°–115° C.(Recrystallized from chloroform-n-hexane).

NMR spectrum (DMSO-$d_6$) δ: 0.5–1.9(38H, broad), 3.54(2H, broad), 4.25(2H, q, $J=7H_Z$), 4.74(1H, d×d), 8.82(1H, broad), 10.93(1H, broad).

Elemental analysis, for $C_{25}H_{45}FN_2O_5$: Calcd. C, 63.53; H, 6.90; N, 5.93. Found: C, 63.48; H, 9.69; N, 5.99.

EXAMPLE 33

A solution comprising 4.40 g. (20 mmoles) of ethyl 5-fluoro-6-hydroxy-1,2,3,4,5,6-hexahydro-2,4-dioxopyrimidine-5-carboxylate, 3.42 g. (40 mmoles) of neopentyl alcohol, 200 mg. of methanesulfonic acid and 25 ml. of dimethoxyethane is heated under reflux for 2 hours. The reaction product is purified by a procedure similar to that described in Example 27 to recover 3.51 g. of ethyl 5-fluoro-6-neopentyloxy-1,2,3,4,5,6-hexahydro-2,4-dioxopyrimidine-5-carboxylate.

Melting Point: 199°–200° C.(Recrystallized from acetone-chloroform-n-hexane).

NMR spectrum (DMSO-$d_6$) δ: 0.80(9H, s), 1.20(3H, t, $J=7H_Z$), 3.25(2H, AB type q), 4.30(2H, q, $J=7H_Z$), 4.80(1H, d×d), 8.78(1H, broad), 10.96(1H, broad).

Elemental analysis, for $C_{12}H_{19}FN_2O_5$: Calcd.: C, 49.65; H, 6.60; N, 9.65. Found: C, 49.66; H, 6.54; N, 9.64.

EXAMPLE 34

A mixture of 4.5 g. of isopropyl 5-fluoro-6-hydroxy-1,2,3,4,5,6-hexahydro-2,4-dioxopyrimidine-5-carboxylate, 70 ml. of isopropyl alcohol, 0.5 g. of p-toluenesulfonic acid and 5.0 g. of anhydrous magnesium sulfate is heated under reflux and stirring for 4 hours. The reaction mixture is filtered and concentrated to dryness under reduced pressure. The resultant white powder is purified by column chromatography on silica gel (solvent:benzene-acetone=4:1) to give 2.8 g. of isopropyl 5-fluoro-6-isopropyloxy-1,2,3,4,5,6-hexahydro-2,4-dioxopyrimidine-5-carboxylate as a white crystalline powder.

Melting Point: 231°–232° C.(decomp.).

NMR spectrum (DMSO-$d_6$) δ: 1.10(6H, d, $J=7H_Z$), 1.23(6H, d, $J=7H_Z$), 3.94(1H, m, $J=7H_Z$), 4.80–5.35(2H, m), 9.85(1H, broad), 10.95(1H, broad).

Elemental analysis, for $C_{11}H_{17}FN_2O_5$: Calcd.: C, 47.82; H, 6.20; N, 10.14. Found: C, 47.75; H, 6.19; N, 9.95.

EXAMPLE 35

In 50 ml. of dioxane is dissolved 3.0 g. of secbutyl 5-fluoro-6-hydroxy-1,2,3,4,5,6-hexahydro-2,4-dioxopyrimidine-5-carboxylate, followed by the addition of 4.0 g. of sec-butyl alcohol, 0.3 g. of p-toluene-sulfonic acid and 4.0 g. of anhydrous magnesium sulfate. With stirring, the mixture is heated under reflux for 10 hours. The reaction mixture is filtered and concentrated to dryness under reduced pressure. The residue is then purified by column chromatography on silica gel (solvent:benzene-acetone=4:1) to give 2.56 g. of secbutyl 5-fluoro-6-sec-butyloxy-1,2,3,4,5,6-hexahydro-2,4-dioxopyrimidine-5-carboxylate as a white powder.

Melting Point: 185°–186° C.

NMR spectrum (DMSO-$d_6$) δ: 0.7–1.9(16H, m), 3.78(1H, m, $J=6.5H_Z$), 4.8–5.3 (2H, m), 8.96(1H, broad), 11.12(1H, broad).

Elemental analysis, for $C_{13}H_{21}FN_2O_5$: Calcd.: C, 51.31; H, 6.96; N, 9.21 Found: C, 51.08; H, 6.87; N, 9.03.

EXAMPLE 36

In n-octyl alcohol is suspended 1.03 g. of methyl 5-fluoro-6-hydroxy-1,2,3,4,5,6-hexahydro-2,4-dioxopyrimidine-5-carboxylate, followed by addition of 130 mg of p-toluenesulfonic acid. With stirring, the reaction is carried out at 150° C. for 3 hours, and then the reaction mixture is evaporated to dryness under reduced pressure. The residue is chromatographed on silica gel (solvent:benzene-acetone=19:1). The crude product thus obtained is recrystallized from benzene-n-hexane to recover 0.49 g. of n-octyl 5-fluoro-6-n-octyloxy-1,2,3,4,5,6-hexahydro-2,4-dioxopyrimidine-5-carboxylate as a white waxy product.

Melting Point: 86.5°–87.50° C.

NMR spectrum (CDCl$_3$) δ: 0.98(6H, broad t, $J=5H_Z$), 1.37(24H, broad s), 3.72(2H, broad), 4.32(2H, t, $J=6H_Z$), 5.00(1H, m), 7.55(1H, broad), 9.20(1H, broad).

Elemental analysis, for $C_{21}H_{37}FN_2O_5$: Calcd.: C, 60.56; H, 8.95; N, 6.73. Found: C, 60.81; H, 9.01; N, 6.61.

EXAMPLE 37

A pressure-resistant reactor of stainless steel with a capacity of 50 ml. is filled with 4.40 g. (20 mmoles) of ethyl 5-fluoro-6-hydroxy-1,2,3,4,5,6-hexahydro-2,4-dioxopyrimidine-5-carboxylate, 1.50 g. (24 mmoles) of ethylmercaptan, a catalytic amount of methanesulfonic acid and 20 ml. of dimethoxyethane and, in an oil bath at 80°–90° C., the contents are magnetically stirred. The contents are concentrated under reduced pressure and the residue is purified as in Example 27 to recover 1.52 g. of ethyl 5-fluoro-6-ethylthio-1,2,3,4,5,6-hexahydro-2,4-dioxopyrimidine-5-carboxylate.

Melting Point: 178°–180° C. (Recrystallized from acetonechloroform-n-hexane).

NMR spectrum (DMSO-d$_6$) δ: 1.18(3H, t, J=7H$_Z$), 1.20(3H, t, J=7H$_Z$), 2.70(2H, q, J=7H$_Z$), 4.27(2H, q, J=7H$_Z$), 5.12(1H, d×d; after addition of deuterium oxide, d, J=6H$_Z$), 8.75(1H, broad), 11.16(1H, broad).

Elemental analysis, for C$_9$H$_{13}$FN$_2$O$_4$S: Calcd.: C, 40.90; H, 4.96; N, 10.60. Found: C, 40.75; H, 4.85; N, 10.57.

EXAMPLE 38

A solution comprising 4.40 g. (20 mmoles) of ethyl 5-fluoro-6-hydroxy-1,2,3,4,5,6-hexahydro-2,4-dioxopyrimidine-5-carboxylate, 3.60 g. (40 mmoles) of tert-butylmercaptan, a catalytic amount of methanesulfonic acid and 40 ml. of dimethoxyethane is heated under reflux for 2 hours. The reaction mixture is concentrated under reduced pressure and the residue is purified as in Example 27 to obtain 2.86 g. of ethyl 5-fluoro-6-tertbutylthio-1,2,3,4,5,6-hexahydro-2,4-dioxopyrimidine-5-carboxylate.

Melting Point: 211°-212° C. (Recrystallized from chloroform-n-hexane).

NMR spectrum (DMSO-d$_6$) δ: 1.22(3H, t, J=7H$_Z$), 1.30(9H, s), 4.30(2H, q, J=7H$_Z$), 5.04(1H, q, J$_{HF}$=12H$_Z$, J$_{HH}$=4H$_Z$), 8.50(1H, broad), 11.06(1H, broad).

Elemental analysis, for C$_{11}$H$_{17}$FN$_2$O$_4$S: Calcd.: C, 45.20; H, 5.86; N, 9.58. Found: C, 45.04; H, 5.77; N, 9.60.

EXAMPLE 39

In 20 ml. of dimethoxyethane is dissolved 3.30 g. (15 mmoles) of ethyl 5-fluoro-6-hydroxy-1,2,3,4,5,6-hexahydro-2,4-dioxopyrimidine-5-carboxylate together with 2.09 g. (18 mmoles) of cyclohexylmercaptan and a catalytic amount of methanesulfonic acid, and the solution is heated under reflux for 1 hour. The reaction product is purified by a procedure similar to that described in Example 27 to give 2.355 g. of ethyl 5-fluoro-6-cyclohexylthio-1,2,3,4,5,6-hexahydro-2,4-dioxopyrimidine-5-carboxylate.

Melting Point: 168°-170° C. (Recrystallized from acetonechloroform-n-hexane).

NMR spectrum (DMSO-d$_6$) δ: 0.9-2.3(13H, broad), 2.92(1H, broad), 4.25(2H, q, J=7H$_Z$), 5.12(1H, q; after addition of deuterium oxide, d, J=8H$_Z$), 8.67(1H, broad), 11.05(1H, broad).

Elemental analysis, for C$_{13}$H$_{19}$FN$_2$O$_4$S: Calcd.: C, 49.04; H, 6.02; N, 8.80. Found: C, 48.68; H, 6.00; N, 8.43.

EXAMPLE 40

In 20 ml of dimethoxyethane is dissolved 3.30 g. (15 mmoles) of ethyl 5-fluoro-6-hydroxy-1,2,3,4,5,6-hexahydro-2,4-dioxopyrimidine-5-carboxylate together with 2.88 g. (16.5 mmoles) of n-decylmercaptan and a catalytic amount of methanesulfonic acid, and the solution is refluxed for 1 hour. The reaction product is purified as in Example 27 to obtain 3.37 g. of ethyl 5-fluoro-6-n-decylthio-1,2,3,4,5,6-hexahydro-2,4-dioxopyrimidine-5-carboxylate.

Melting Point: 107°-108° C. (Recrystallized from acetonechloroform-n-hexane).

NMR spectrum (DMSO-d$_6$) δ: 0.80-1.95(22H, broad), 2.80(2H, broad), 4.42(2H, q, J=7H$_Z$), 5.30(1H, q), 8.90(1H, broad), 11.25(1H, broad).

Elemental analysis, for C$_{17}$H$_{29}$FN$_2$O$_4$S: Calcd.: C, 54.23; H, 7.76; N, 7.44. Found: C, 54.50; H, 7.87; N, 7.49.

EXAMPLE 41

A solution consisting of 3.30 g. (15 mmoles) of ethyl 5-fluoro-6-hydroxy-1,2,3,4,5,6-hexahydro-2,4-dioxopyrimidine-5-carboxylate, 4.30 g. (15 mmoles) of n-octadecylmercaptan, a catalytic amount of methanesulfonic acid and 30 ml. of dimethoxyethane is heated under reflux for 1 hour. The reaction product thus obtained is purified as in Example 27 to give 3.30 g. of ethyl 5-fluoro-6-n-octadecylthio-1,2,3,4,5,6-hexahydro-2,4-dioxopyrimidine-5-carboxylate.

Melting Point: 114°-115° C. (Recrystallized from chloroform-n-hexane).

NMR spectrum (DMSO-d$_6$) δ: 0.6-2.0(38H, broad), 2.65(2H, broad), 4.22(2H, q, J=7H$_Z$), 5.04(1H, q), 8.65(1H, broad), 10.97(1H, broad).

Elemental analysis, for C$_{25}$H$_{45}$FN$_2$O$_4$S: Calcd.: C, 61.44; H, 9.28; N, 5.73. Found: C, 61.45; H, 9.41; N, 5.66.

EXAMPLE 42

A solution consisting of 2.06 g. (10 mmoles) of methyl 5-fluoro-6-hydroxy-1,2,3,4,5,6-hexahydro-2,4-dioxopyrimidine-5-carboxylate, 2.20 g. (20 mmoles) of thiophenol, a catalytic amount of methanesulfonic acid and 20 ml. of dimethoxyethane is heated under reflux for 2 hours. The reaction product is purified as in Example 27 to recover 2.57 g. of methyl 5-fluoro-6-phenylthio-1,2,3,4,5,6-hexahydro-2,4-dioxopyrimidine-5-carboxylate.

Melting Point: 173°-176° C. (Recrystallized from acetonechloroform-n-hexane).

NMR spectrum (DMSO-d$_6$) δ: 3.75(3H, s), 5.38(1H, t, J=3H$_Z$), 7.40(5H, broad s), 8.83(1H, broad), 11.11(1H, broad).

Elemental analysis, for C$_{12}$H$_{11}$FN$_2$O$_4$S: Calcd.: C, 48.32; H, 3.72; N, 9.39. Found: C, 48.16; H, 3.60; N, 9.53.

EXAMPLE 43

In 30 ml. of methanol is dissolved 1.00 g. of methyl 6-acetoxy-5-fluoro-1,2,3,4,5,6-hexahydro-2,4-dioxopyrimidine-5-carboxylate and the solution is refluxed on an oil bath for 1 hour. The reaction mixture is allowed to cool and concentrated under reduced pressure to about 10 ml, followed by dilution with 15 ml. of chloroform and 30 ml. of n-hexane to give 679 mg. of methyl 5-fluoro-6-methoxy-1,2,3,4,5,6-hexahydro-2,4-dioxopyrimidine-5-carboxylate as colorless needles. In addition, the mother liquor yields 150 mg. colorless needles. Total yield 829 mg.

EXAMPLE 44

In 50 ml. of ethanol is dissolved 2.40 g. of n-octyl 6-acetoxy-5-fluoro-1,2,3,4,5,6-hexahydro-2,4-dioxopyrimidine-5-carboxylate and the solution is heated under reflux for 5 hours. The solvent is distilled off to recover 2.48 g. of residue. The residue is recrystallized from chloroform-n-hexane to obtain 1.93 g. of white needles. The mother liquor is chromatographed on silica gel (solvent:chloroform-ethyl acetate=1:1 (V/V)) to recover the second crop of 0.26 g. of white powder. This procedure thus yields a total of 2.19 g. of n-octyl 5-fluoro-6-ethoxy-1,2,3,4,5,6-hexahydro-2,4-dioxopyrimidine-5-carboxylate.

Melting Point: 127°-128° C. (Recrystallized from chloroform-n-hexane).

NMR spectrum (DMSO-d$_6$) δ: 0.63-1.93(18H, m), 3.33-3.98(2H, m), 4.25(2H, m), 4.81(1H, d×d, J=5 and $2H_Z$; after addition of deuterium oxide, d, J=2H$_Z$), 8.82, 10.95(each 1H, broad).

Elemental analysis, for C$_{12}$H$_{25}$FN$_2$O$_5$: Calcd.: C, 54.21; H, 7.58; N, 8.43. Found: C, 54.10; H, 7.59; N, 8.38.

EXAMPLE 45

In a mixture of 10 ml of acetone and 2.0 ml of water is dissolved 1.30 g. of n-octyl 6-acetoxy-5-fluoro-1,2,3,4,5,6-hexahydro-2,4-dioxopyrimidine-5-carboxylate, followed by addition of 0.3 ml. of pyridine. The mixture is stirred at room temperature overnight and, then, concentrated to dryness under reduced pressure, whereby 1.05 g. of white solid is obtained. To this solid is added 5 ml. of chloroform and, after stirring, the insolubles are recovered by filtration and dissolved in acetone. The insolubles are filtered off and the filtrate is concentrated to dryness under reduced pressure, whereupon 0.85 g. of residue is obtained. This residue is chromatographed on silica gel (solvent:benzene-acetone=2:1 (V/V)) to obtain 675 mg. of n-octyl 5-fluoro-6-hydroxy-1,2,3,4,5,6-hexahydro-2,4-dioxopyrimidine-5-carboxylate.

Melting Point: 157°–8° C. (Recrystallized from acetonechloroform-hexane).

NMR spectrum (DMSO-d$_6$) δ: 0.67–1.83(15H, m), 4.22(2H, approx. triplet, J=6H$_Z$), 4.88(1H, m; after addition of deuterium oxide, d, J=3H$_Z$), 7.14(1H, d, J=5H$_Z$), 8.56, 10.56(each 1H, broad).

Elemental analysis, for C$_{13}$H$_{21}$FN$_2$O$_5$.1/4H$_2$O: Calcd.: C, 50.56; H, 7.02; N, 9.07. Found: C, 50.29; H, 6.77; N, 8.82.

EXAMPLE 46

In 10 ml. of acetone is dissolved 300 mg. of methyl 6-acetoxy-5-fluoro-1,2,3,4,5,6-hexahydro-2,4-dioxopyrimidine-5-carboxylate, followed by dropwise addition of 200 mg. of piperidine. The reaction mixture is allowed to stand at room temperature for 5 hours and the solvent is removed under reduced pressure, which leaves a yellow vitreous solid. This solid is subjected to column chromatography on silica gel (solvent:-chloroform-ethyl acetate=2:1 (V/V)) and the fractions rich in the desired compound are concentrated under reduced pressure to recover a colorless vitreous solid. This is recrystallized from acetone-n-hexane to give 162 mg. of methyl 5-fluoro-6-(1-piperidino)-1,2,3,4,5,6-hexahydro-2,4-dioxopyrimidine-5-carboxylate as colorless needles.

NMR spectrum (DMSO-d$_6$) δ: 1.45(6H, m), 2.60(4H, m), 4.53(1H, d×d, J$_{HF}$=4H$_Z$, J=5H$_Z$; after addition of deuterium oxide, d, J$_{HF}$=4H$_Z$), 8.23(1H, broad), 10.90(1H, broad).

Melting Point: 142°–144° C. (Recrystallized from chloroform).

Elemental analysis, for C$_{11}$H$_{16}$FN$_3$O$_4$: Calcd.: C, 48.35; H, 5.90; N, 15.38; F, 6.95. Found: C, 48.29; H, 5.67; N, 15.64; F, 7.01.

EXAMPLE 47

In 5 ml. of acetone is dissolved 0.618 g. (3 mmoles) of methyl 5-fluoro-6-hydroxy-1,2,3,4,5,6-hexahydro-2,4-dioxopyrimidine-5-carboxylate and, under ice-cooling and stirring, 1 ml. of acetic anhydride and 1 ml. of pyridine are added. The mixture is reacted at the same temperature overnight. The low-boiling fractions are distilled off under reduced pressure and the residue is passed through a column of neutral alumina (solvent-:acetone-benzene=1:4 (V/V)) to recover 0.63 g. of a colorless solid. Based on its NMR spectrum, this product is identified as methyl 6-acetoxy-5-fluoro-1,2,3,4,5,6-hexahydro-2,4-dioxopyrimidine-5-carboxylate.

EXAMPLE 48

In a mixture of 5 ml. acetone and 1 ml. pyridine is dissolved 1.03 g. (5 mmoles) of methyl 5-fluoro-6-hydroxy-1,2,3,4,5,6-hexahydro-2,4-dioxopyrimidine-5-carboxylate and, under ice-cooling and stirring, 0.773 g. (5.5 mmoles) of benzoyl chloride is added dropwise. The reaction is further allowed to take place at room temperature overnight. The volatiles are distilled off under reduced pressure and the residue is passed through a short column of neutral alumina (solvent:acetone-benzene=1:4 (V/V)) to obtain 1.21 g. of methyl 6-benzoyloxy-5-fluoro-1,2,3,4,5,6-hexahydro-2,4-dioxopyrimidine-5-carboxylate.

NMR spectrum (DMSO-d$_6$) δ: 3.94(3H, s), 6.48(1H, m), 7.2–8.1(5H, m), 9.20(1H, broad), 11.37(1H, broad).

EXAMPLE 49

In 400 ml. of acetic acid is suspended 2.1 g. of 1,2,3,4-tetrahydro-2,4-dioxopyrimidine-5-carboxamide and, with intensive stirring, 1.5 molar equivalents of fluorine gas previously diluted with 9 times its volume of nitrogen (gas) is introduced at room temperature over a period of 6 hours. The reaction mixture is then concentrated to recover a crude product of 6-acetoxy-5-fluoro-1,2,3,4,5,6-hexahydro-2,4-dioxopyrimidine-5-carboxamide.

NMR spectrum (DMSO-d$_6$) δ: 2.10(3H, s), 6.12(1H, broad d, J=5H$_Z$), 8.0(1H, broad), 8.2(1H, broad), 9.1(1H, broad), 11.1 (1H, broad).

This crude 6-acetoxy compound is dissolved in 100 ml. of ethanol and the solution is refluxed for 2 hours, then cooled. Crystals separated are collected by filtration and the filtrate is concentrated to give another crop of crystalls which are collected by filtration. Both crystalline products are combined and recrystallized from ethanol to give 1.7 g. of 5-fluoro-6-ethoxy-1,2,3,4,5,6-hexahydro-2,4-dioxopyrimidine-5-carboxamide as colorless prisms.

Melting Point: 224°–226° C. (decomp.).

NMR spectrum (DMSO-d$_6$) δ: 0.90–1.32(4.5H, m), 3.30–3.88(3H, m), 4.78(1H, broad d, J=4H$_Z$), 7.84(1H, broad), 8.06(1H, broad), 8.75(1H, broad), 10.55(1H, broad).

Elemental analysis, for C$_7$H$_{10}$FN$_3$O$_4$.1/2C$_2$H$_5$OH: Calcd.: C, 39.67; H, 5.41; N, 17.35. Found: C, 39.44; H, 5.37; N, 17.37.

EXAMPLE 50

In 15 ml. of dimethoxyethane is dissolved 1.03 g. (5 mmoles) of methyl 5-fluoro-6-hydroxy-1,2,3,4,5,6-hexahydro-2,4-dioxopyrimidine-5-carboxylate. To this solution are added 1.03 g. (10 mmoles) of benzyl alcohol and a catalytic amount of methanesulfonic acid. The mixture is heated on reflux for 2 hours. The reaction mixture is concentrated under reduced pressure and the residue is purified by a procedure similar to that described in Example 27 to give 0.80 g. of methyl 6-benzyloxy-5-fluoro-1,2,3,4,5,6-hexahydro-2,4-dioxopyrimidine-5-carboxylate.

Melting Point: 173°–174° C. (Recrystallized from acetone-chloroform).

NMR spectrum (DMSO-d$_6$) δ: 4.68(2H, s), 3.80(3H, s), 4.98(1H, d×d), 7.34(5H, broad s), 9.00(1H, broad), 11.08(1H, broad).

Elemental analysis, for $C_{13}H_{13}FN_2O_5$: Calcd.: C, 52.71; H, 4.42; N, 9.46. Found.: C, 52.50; H, 4.28; N, 9.35.

EXAMPLE 51

In 150 ml. of acetic acid is suspended 1.05 g. of 1,2,3,4-tetrahydro-2,4-dioxopyrimidine-5-(N,N-diethyl)carboxamide, followed by the passage of fluorine gas previously diluted with 9 times its volume of nitrogen (gas) at room temperature. When 2.8 molar equivalents of fluorine has been introduced based on the substrate (over a period of 6.5 hours), the reaction mixture is evaporated to dryness under reduced pressure, whereby a pale yellow syrupy residue is obtained. This residue is dissolved in 50 ml. of water and the solution is stirred at room temperature for 2 hours, followed by concentration to dryness under reduced pressure. The resultant viscous product is subjected to column chromatography on silica gel (solvent:benzene-aceteone=2:1) to recover 0.39 g. of white powder. The powder is recrystallized from ethyl acetate to obtain 0.12 g. of 5-fluoro-6-hydroxy-1,2,3,4,5,6-hexahydro-2,4-dioxopyrimidine-5-(N,N-diethyl)carboxamide as white microfine crystals.

Melting Point: 190°–192° C. (decomp.).

NMR spectrum (DMSO-$d_6$) δ: 0.9–1.4(6H, m), 3.1–3.8(4H, m), 5.04(1H, t, J=5H$_Z$), 6.97(1H, d, J=5H$_Z$), 8.5(1H, broad), 10.76(1H, broad).

Elemental analysis, for $C_9H_{14}FN_3O_4$: Calcd.: C, 43.72; H, 5.71; N, 17.00. Found: C, 43.61; H, 5.57; N, 16.98.

EXAMPLE 52

In 10 ml. of ethanol containing 20% of hydrogen chloride is dissolved 0.30 g. of 5-fluoro-6-hydroxy-1,2,3,4,5,6-hexahydro-2,4-dioxopyrimidine-5-carbonitrile, followed by addition of 1.0 g. of silica gel for chromatography. The mixture is stirred at room temperature for 20 hours. The reaction mixture is evaporated to dryness under reduced pressure and subjected to chromatography on silica gel (solvent:chloroform-ethanol=12:1) to recover 0.27 g. of ethyl 5-fluoro-6-ethoxy-1,2,3,4,5,6-hexahydro-2,4-dioxopyrimidine-5-carboxylate.

EXAMPLE 53

A solution consisting of 3.30 g. (15 mmoles) of ethyl 5-fluoro-6-hydroxy-1,2,3,4,5,6-hexahydro-2,4-dioxopyrimidine-5-carboxylate, 2.05 g. (16.5 mmoles) of benzylmercaptan, a catalytic amount of methanesulfonic acid and 20 ml. of dimethoxyethane is heated under reflux for 1 hour. The reaction mixture is then purified as in Example 27 to give 2.23 g. of ethyl 6-benzylthio-5-fluoro-1,2,3,4,5,6-hexahydro-2,4-dioxopyrimidine-5-carboxylate.

Melting Point: 149°–150° C. (Recrystallized from chloroform-n-hexane).

NMR spectrum (DMSO-$d_6$) δ: 1.16(3H, t, J=7H$_Z$), 3.96(2H, s), 4.25(2H, q, J=7H$_Z$), 5.02(1H, d×d; after addition of deuterium oxide, d, $J_{HF}$=7H$_Z$), 7.30(5H, s), 8.85(1H, broad), 11.18 (1H, broad)

Elemental analysis, for $C_{14}H_{15}FN_2O_4S$: Calcd.: C, 51.53; H, 4.63; N, 8.58; F, 5.82. Found: C, 51.51; H, 4.47; N, 8.73; F, 5.84.

EXAMPLE 54

A pressure-resistant vessel of stainless steel with a capacity of 50 ml. is charged with 3.30 g. (15 mmoles) of ethyl 5-fluoro-6-hydroxy-1,2,3,4,5,6-hexahydro-2,4-dioxopyrimidine-5-carboxylate, 1.33 g. (18 mmoles) of allylmercaptan, a catalytic amount of methanesulfonic acid and 20 ml. of dimethoxyethane and, heated in an oil bath at 80°–90° C. for one hour, while the contents are magnetically stirred. The contents are concentrated under reduced pressure and the residue is purified as in Example 27 to give 1.28 g. of ethyl 6-allylthio-5-fluoro-1,2,3,4,5,6-hexahydro-2,4-dioxopyrimidine-5-carboxylate.

Melting Point: 122°–123° C. (Recrystallized from chloroform-n-hexane).

NMR spectrum (DMSO-$d_6$) δ: 1.20(3H,t,J=7H$_Z$), 3.36(2H,2 peaks), 4.30(2H,q,J=7H$_Z$), 4.75–6.20(4H, m), 8.77(1H, broad), 11.15(1H, broad).

Elemental analysis, for $C_{10}H_{13}FN_2O_4S$: Calcd.: C, 43.47; H, 4.74; N, 10.14; F, 6.88. Found: C, 43.52; H, 4.44; N, 10.12; F, 6.90.

EXAMPLE 55

A solution consisting of 3.30 g. (15 mmoles) of ethyl 5-fluoro-6-hydroxy-1,2,3,4,5,6-hexahydro-2,4-dioxopyrimidine-5-carboxylate, 2.40 g. (15 mmoles) of 2-naphthalenethiol, a catalytic amount of methanesulfonic acid and 25 ml. of dimethoxyethane is heated under reflux for 1 hour and the reaction product is purified as in Example 27 to give 1.71 g. of ethyl 5-fluoro-6β-naphthylthio-1,2,3,4,5,6-hexahydro-2,4-dioxopyrimidine-5-carboxylate.

Melting Point: 198°–201° C. (Recrystallized from acetone-chloroform-n-hexane).

NMR spectrum (DMSO-$d_6$) δ: 1.16(3H, t, J=7H$_Z$), 4.27(2H, q, J=7H$_Z$), 5.55(1H, t, J=4H$_Z$; after addition of deuterium oxide, d, $J_{HF}$=4H$_Z$), 7.1–8.2(7H, m), 8.90(1H, broad), 11.18(1H, broad).

Elemental analysis, for $C_{17}H_{15}FN_2O_4S$: Calcd.: C, 56.35; H, 4.41; N, 7.73; F, 5.24. Found: C, 56.38; H, 4.06; N, 8.01; F, 5.07.

EXAMPLE 56

In 20 ml. of acetone is dissolved 4.40 g. of ethyl 5-fluoro-6-hydroxy-1,2,3,4,5,6-hexahydro-2,4-dioxopyrimidine-5-carboxylate, followed by the addition of 2.5 ml. of acetic anhydride. To this is further added dropwise 2 ml. of pyridine and the mixture is allowed to stand at room temperature for 24 hours. To the colorless reaction mixture thus obtained is added dropwise 5.9 ml. of piperidine, whereby the reaction takes place with evolution of heat. After 5.5 hours' standing at room temperature, volatiles are distilled off under reduced pressure and the yellow oily residue is dissolved in chloroform. The solution is subjected to column chromatography on silica gel (80 g., solvent:-chloroform). The fractions rich in the desired compound are concentrated under reduced pressure to recover 5.20 g. of a white solid. Upon recrystallization from chloroform-hexane, 3.0 g. of ethyl 5-fluoro-6-piperidino-1,2,3,4,5,6-hexahydro-2,4-dioxopyrimidine-5-carboxylate is obtained as colorless needles.

Melting Point: 149°–150° C.

Elemental analysis, for $C_{12}H_{18}FN_3O_4$: Calcd.: C, 50.17; H, 6.31; N, 14.63. Found: C, 50.11; H, 6.38; N, 14.60.

NMR spectrum (DMSO-$d_6$) δ: 1.25(3H, t, J=7H$_Z$), 1.43(6H, m), 2.57(4H, m), 4.28(2H, q, J=7H$_Z$), 4.52(1H, d×d, $J_{HF}$=4H$_Z$, J=6H$_Z$; after addition of deuterium oxide, d, $J_{HF}$=4H$_Z$), 8.30(1H, broad), 10.93(1H, broad).

EXAMPLE 57

In 20 ml. of acetone is dissolved 4.40 g. of ethyl 5-fluoro-6-hydroxy-1,2,3,4,5,6-hexahydro-2,4-dioxopyrimidine-5-carboxylate, followed by addition of 2.5 ml. of acetic anhydride. To this is further added dropwise 2 ml. of pyridine, and the mixture is allowed to stand at room temperature for 24 hours. To the resultant colorless reaction mixture is added dropwise 5.1 ml. of diethylamine, whereby the reaction takes place with evolution of heat. After 7.5 hours' standing at room temperature, volatiles are distilled off under reduced pressure and the yellow oily residue is dissolved in chloroform. The solution is subjected to column chromatography on silica gel (70 g.; solvent:chloroform-methanol=60/1 (V/V)) and the fractions rich in the desired compound are concentrated under reduced pressure to give 4.10 g. of ethyl 5-fluoro-6-diethylamino-1,2,3,4,5,6-hexahydro-2,4-dioxopyrimidine-5-carboxylate as a pale yellow salid.

NMR spectrum (DMSO-$d_6$) δ: 0.97(6H, t×2, J=6Hz), 1.25(3H, t, J=7Hz), 2.67 (4H, q×2, J=7Hz), 4.27(2H, q, J=7Hz), 4.77(1H, d×d, J=2Hz, $J_{HF}$=16Hz; after addition of deuterium oxide, d, $J_{HF}$=16Hz), 8.25(1H, broad), 10.7(1H, broad).

EXAMPLE 58

In 20 ml. of acetone is dissolved 4.40 g. of ethyl 5-fluoro-6-hydroxy-1,2,3,4,5,6-hexahydro-2,4-dioxopyrimidine-5-carboxylate, followed by addition of 2.5 ml. of acetic anhydride. To this is further added dropwise 2 ml. of pyridine, and the mixture is allowed to stand at room temperature for 24 hours. To the resultant colorless reaction mixture is added 5.0 ml. of n-butylamine, whereby the reaction takes place with evolution of heat to yield a brown-colored solution. This solution is allowed to stand at room temperature for 4 hours then volatiles are distilled off under reduced pressure. The brown oily residue is dissolved in chloroform and subjected to column chromatography (70 g.; solvent:-chloroform). The fractions rich in the desired compound are concentrated under reduced pressure to obtain a yellowish brown solid, which is recrystallized from chloroform-hexane to give 3.0 g. of ethyl 6-n-butylamino-5-fluoro-1,2,3,4,5,6-hexahydro-2,4-dioxopyrimidine-5-carboxylate as colorless needles.

Melting Point: 112°–113° C.

NMR spectrum (DMSO-$d_6$) δ: 0.87(3H, m), 1.23(3H, t, J=7Hz), 1.23(4H, m), 2.25(1H, m), 2.53(2H, m), 4.28(2H, q, J=7Hz), 4.50(1H, m; after addition of deuterium oxide, d, $J_{HF}$=9Hz), 9.0(2H, broad).

Elemental analysis, for $C_{11}H_{18}FN_3O_4$: Calcd.: C, 47.99; H, 6.59; N, 15.27. Found: C, 47.59; H, 6.63; N, 15.18.

EXAMPLE 59

In 20 ml. of acetone is dissolved 4.40 g. of ethyl 5-fluoro-6-hydroxy-1,2,3,4,5,6-hexahydro-2,4-dioxopyrimidine-5-carboxylate, followed by addition of 2.5 ml. of acetic anhydride. To this is added dropwise 2 ml. of pyridine, and the mixture is allowed to stand at room temperature for 24 hours. To the resultant colorless reaction mixture is added 5.5 ml. of benzylamine, whereby the reaction takes place with evolution of heat. The reaction mixture is allowed to stand at room temperature for 3 hours, whereupon crystals separate out. The crystals are recovered by filtration, washed with chloroform and recrystallized from ethyl acetate to give 4.1 g. of ethyl 6-benzylamino-5-fluoro-1,2,3,4,5,6-hexahydro-2,4-dioxopyrimidine-5-carboxylate as colorless flakes.

Melting Point: 157°–158° C.

NMR spectrum (DMSO-$d_6$) δ: 1.20(3H, t, J=7Hz), 3.03(1H, m), 3.87(2H, m), 4.23(2H, q, J=7Hz), 4.52(1H, m; after addition of deuterium oxide, d, $J_{HF}$=10Hz), 7.28(5H, m), 8.43 (1H, broad), 10.92(1H, broad).

Elemental analysis, for $C_{14}H_{16}FN_3O_4$: Calcd.: C, 54.36; H, 5.22; N, 13.59. Found: C, 54.22; H, 5.17; N, 13.65.

EXAMPLE 60

4.40 g. of ethyl 5-fluoro-6-hydroxy-1,2,3,4,5,6-hexahydro-2,4-dioxopyrimidine-5-carboxylate is acetylated in the manner similar to that described in Example 56, followed by the addition of 20 ml. of aniline and 20 ml. of pyridine to the reaction mixture. The mixture is allowed to stand at room temperature for 6 days. The yellow reaction mixture is concentrated under reduced pressure, whereupon an oily residue is obtained. The residue is dissolved in chloroform and subjected to column chromatography on silica gel (30 g.; solvent:-chloroform). The fractions rich in the desired compound are concentrated under reduced pressure to recover a yellow oil, which is dissolved in acetone. Addition of benzene and n-hexane to the acetone solution yields 4.83 g of colorless needles of ethyl 6-anilino-5-fluoro-1,2,3,4,5,6-hexahydro-2,4-dioxopyrimidine-5-carboxylate.

NMR spectrum (DMSO-$d_6$) δ:
1.22(3H, t, J=7Hz), 4.28(2H, q, J=7Hz), 5.33(1H, d×3, J=4Hz, 10Hz; after addition of deuterium oxide, d, $J_{HF}$=10Hz), 6.5–7.4(6H, m), 8.48(1H, broad), 11.02(1H, broad).

EXAMPLE 61

In 15 ml. of water is dissolved 30 mg. of methyl 5-fluoro-1-(2-tetrahydrofuryl)-6-hydroxy-1,2,3,4,5,6-hexahydro-2,4-dioxopyrimidine-5-carboxylate and the solution is cooled in an ice-water bath. To this solution is added 1 ml. of trifluoroacetic acid and the mixture is left standing in a refrigerator. 5-Fluoro-1-(2-tetrahydrofuryl)uracil formed can be quantitatively determined spectrophotometrically ($\lambda_{max}^{pH\ 1.0}$ 272 mm, (ε 9000)).

After 10 days: 29%
After 14 days: 41%
After 21 days: 58%
After 31 days: 73%
After 46 days: 84%

After 46 days, the reaction mixture is neutralized with sodium bicarbonate and subjected to thin-layer chromatography (silica gel; solvent:chloroform-methanol=6/1 (V/V)). The chromatogram revealed the presence of a product which agreed with an authentic sample of Futrafur ®.

EXAMPLE 62

In 10 ml. of water is dissolved 27 mg. of methyl 5-fluoro-1-(2-tetrahydrofuryl)-6-hydroxy-1,2,3,4,5,6-hexahydro-2,4-dioxopyrimidine-5-carboxylate and, under cooling in an ice-water bath, 4.5 ml. of 1 N hydrochloric acid is added. The solution is allowed to stand in a refrigerator. The Futrafur ® formed is quantitatively determinable spectrometrically ($\lambda_{max}^{pH\ 1.0}$ 272 mm (ε=9000)).

After 7 days: 16%

After 10 days: 28%
After 16 days: 49%
After 31 days: 69%

After 31 days, the reaction mixture is neutralized with sodium bicarbonate and subjected to thin-layer chromatography on silica gel (solvent:chloroform-methanol=6/1 (V/V)). The chromatogram revealed a single spot corresponding to an authentic sample of Futrafur ®.

REFERENCE EXAMPLE 1

In 750 ml. of dry dimethylformamide is suspended 156 g. of 1,2,3,4-tetrahydro-2,4-dioxopyrimidine-5-carboxylic acid and, to this suspension, 238 g. of thionyl chloride is added with stirring at a temperature not exceeding 50° C. over one hour and 10 minutes. The reaction mixture is then warmed at 45°–50° C. for 1 hour and at 50°–60° C. for another hour. The mixture is allowed to stand at room temperature overnight and the resultant precipitate is recovered by filtration. It is washed with dry dimethylformamide and, then, with benzene, followed by drying at 80° C. and under reduced pressure. By this procedure is obtained 210 g. of 1,2,3,4-tetrahydro-2,4-dioxopyrimidine-5-carbonyl chloride.dimethylformamide.hemi-hydrogen chloride complex as a white powder.

Melting Point: 180° C. (decomp.)

Elemental analysis, for $C_8H_{10}ClN_3O_4\cdot\frac{1}{2}HCl$: Calcd.: C, 36.14; H, 3.98; N, 15.80. Found: C, 36.04; H, 3.73; N, 15.82.

NMR spectrum (DMSO-$d_6$) δ: 2.7(3H, s), 2.87(3H, s), 7.88(1H, s), 8.18(1H, broad), 11.77–12.2(1H, broad), 13.4(1H, broad).

REFERENCE EXAMPLE 2

Synthesis of 1,2,3,4-tetrahydro-2,4-dioxopyrimidine-5-carboxylic acid esters General procedure: In 50–100 ml. of dry toluene is suspended 13.3 g. of 1,2,3,4-tetrahydro-2,4-dioxopyrimidine-5-carbonyl chloride.dimethylformamide.hemi-hydrogen chloride complex, followed by the addition of 1.1 molar equivalents of the corresponding alcohol or phenol. The mixture is heated under reflux for 20 minutes. After cooling, the precipitate is recovered by filtration, washed with a solvent such as toluene, acetone, or ether and dried to obtain a 1,2,3,4-tetrahydro-2,4-dioxopyrimidine-5-carboxylic acid ester. In many instances, the product thus obtained is pure enough for its use directly as a starting material in the next process.

The following may be mentioned as examples of the novel esters that can be produced in the above manner.

General formula 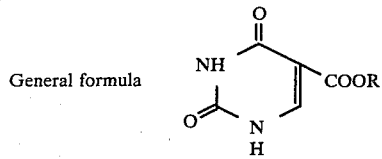

| R = | Recrystallization solvent | m.p. (°C.) |
| --- | --- | --- |
| n-Propyl | Water | 231–232 |
| i-Propyl | Water | 243–244 (decomp.) |
| i-Butyl | Water | 253–254 |

-continued

General formula 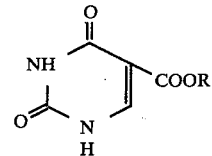

| R = | Recrystallization solvent | m.p. (°C.) |
| --- | --- | --- |
| sec-Butyl | Water | (decomp.) 225–226 |
| n-Amyl | Water | 228–229 |
| n-Hexyl | Water | 196–199 |
| n-Heptyl (hemihydrate) | Dioxane | 210–216 |
| n-Octyl | Dioxane | 224–226 |
| n-Stearyl | Dioxane | 206–207 |
| 2-Chloroethyl | Water | 245–246 (decomp.) |
| 2,2,2-Trifluoroethyl | Water | 263–286 (with evaporation) |
| Benzyl | Water | 243–244 (decomp.) |
| Cyclohexyl | Water | 235(decomp.) |
| Phenyl (+½ dioxane) | Dioxane | 272(decomp.) |
| 1-Ethoxycarbonylethyl | Water | 171–173 |

REFERENCE EXAMPLE 3

In 20 ml. of toluene is suspended 6.0 g. of 1,2,3,4-tetrahydro-2,4-dioxopyrimidine-5-carboxylic acid, followed by addition of 7 ml. of piperidine. With stirring and under heating, 4 ml. of phosphorus oxychloride is added dropwise and the mixture is refluxed for 30 minutes. After cooling, the toluene is decanted off and the residue is boiled with 50 ml. of water. The resultant crystalline precipitate is recovered by filtration and recrystallized from 50 ml. of water to give 2.3 g. of N-(1,2,3,4-tetrahydro-2,4-dioxopyrimidine-5-carbonyl)-piperidine as white flakes.

Melting Point: 294°–295° C. (decomp.).

REFERENCE EXAMPLES 4–6

By a procedure similar to that described above, the following compounds are obtained.

N-(1,2,3,4-tetrahydro-2,4-dioxopyrimidine-5-carbonyl)morpholine, melting point: 306°–307° C. (decomp.), white microfine crystals.

1,2,3,4-Tetrahydro-2,4-dioxopyrimidine-5-(N,N-diethyl)-carboxamide, melting point: 248°–249° C. (decomp.), pale yellow prisms.

1,2,3,4-Tetrahydro-2,4-dioxopyrimidine-5-(N-phenyl)carboxamide, melting point: 359°–360° C. (decomp.), pale yellow powder.

REFERENCE EXAMPLE 7

A mixture of 5 g. of methyl 1,2,3,4-tetrahydro-2,4-dioxopyrimidine-5-carboxylate, 50 ml. of DMF and 20 ml. of benzylamine is heated at 130° C. for 7 hours and then the reaction mixture is concentrated under reduced pressure. To the residue is added water and the solid precipitate is recovered by filtration and washed with ethanol to give 2.2 g. of 1,2,3,4-tetrahydro-2,4-dioxopyrimidine-5-(N-benzyl)-carboxamide as white flakes.

Melting Point: 321°–322° C. (decomp.).

REFERENCE EXAMPLE 8

In 7 ml. of acetic acid is suspended 1.3 g. of 1,2,3,4-tetrahydro-2,4-dioxopyrimidine-5-carbonitrile, followed by the addition of 0.7 g. tert-butyl alcohol and 1.0 g. of sulfuric acid. The mixture is stirred at room temperature for 2 days. To the reaction mixture white with turbidity is added 20 g. of ice-water and the precipitate is recovered by filtration, rinsed with water then dried to give 1.2 g. of 1,2,3,4-tetrahydro-2,4-dioxopyrimidine-5-(N-tert-butyl)-carboxamide as a white powder.

Melting Point: 310°–311° C. (decomp.).

REFERENCE EXAMPLE 9

A glass reaction vessel of a capacity of 200 ml. is charged with 15.3 g. of N-methylurea, 30.1 g. of ethyl formate ortho-ester and 27.1 g. of dimethyl malonate and heated in an oil bath at 135° C. under vigorous stirring. The N-methylurea dissolved to yield a homogeneous solution. After a while, colorless flakes separate. Ethanol formed is expelled by distillation over a period of about 50 minutes. After cooling, the crystals are recovered by filtration, washed with ethanol and then with hexane.

By the NMR spectrum, this product is confirmed to be N,N'-bis-(methylcarbamoyl)formamidine. Yield: 4.9 g.

NMR spectrum (DMSO-$d_6$) δ: 2.67(6H, d, J=5$H_Z$), 7.20(2H, broad), 8.73(1H, s), 9.80(1H, broad).

An additional crop of colorless needles is obtained from the mother liquor. These crystals are subjected to column chromatography on silica gel to recover 6.5 g. colorless needles of dimethyl N-(N-methylcarbamoyl)aminomethylenemalonate.

NMR spectrum (DMSO-$d_6$) δ: 2.73(3H, d, J=4.5$H_Z$), 3.67(3H, s), 3.72(3H, s), 7.97(1H, broad), 8.50(1H, d, J=12$H_Z$), 10.37(1H, d, J=12$H_Z$).

REFERENCE EXAMPLE 10

In 120 ml. of methanol is suspended 11.35 g. of dimethyl N-(N-methylcarbamoyl)aminomethylenemalonate, followed by addition of 15 ml. of a 28% methanolic solution of sodium methoxide. The mixture is stirred at room temperature for a while. After the starting material has dissolved to yield a homogeneous solution, the mixture is heated under reflux for 20 minutes. In the course of reflux, a precipitate separates. After cooling, 80 ml. of 1N hydrochloric acid is added to acidify the mixture, whereupon the precipitate turns into crystals. After ice-cooling, the crystals are recovered by filtration, washed with water and then with acetone, and dried in air to give 6.59 g. of methyl 3-methyl-1,2,3,4-tetrahydro-2,4-dioxopyrimidine-5-carboxylate as colorless needles. Recrystallization from water yields 4.28 g. of the pure material as colorless flakes, melting point: 262°–264° C.

EXAMPLE 63

In 50 ml. of dimethoxyethane is dissolved 8.80 g. of ethyl 5-fluoro-6-hydroxy-1,2,3,4,5,6-hexahydro-2,4-dioxopyrimidine-5-carboxylate, followed by the addition of 6.0 g. of 2,2,2-trifluoroethanol and a catalytic amount of methanesulfonic acid. The mixture is heated under reflux for 1.5 hours. The solvent is distilled off under reduced pressure and the residue is treated as in Example 27 to give 1.54 g. of ethyl 5-fluoro-6-(2,2,2-trifluoro)ethoxy)-1,2,3,4,5,6-hexahydro-2,4-dioxopyrimidine-5-carboxylate as a white powder.

Melting Point: 166°–173° C.

NMR spectrum (DMSO-$d_6$) δ: 1.22(3H, t, J=7$H_Z$), 4.27(2H, q, J=9$H_Z$), 4.30(2H, q, J=7$H_Z$), 5.15(1H, d×d; after addition of deuterium oxide, d, J=2$H_Z$), 8.35(1H, broad), 10.53 (1H, broad).

EXAMPLE 64

In 20 ml. of 1 N aqueous sodium hydroxide solution is dissolved 102.15 mg. of methyl 5-fluoro-6-methoxy-1,2,3,4,5,6-hexahydro-2,4-dioxopyrimidine-5-carboxylate and the solution is allowed to stand at room temperature for 1 hour. The reaction mixture is made acidic with 1.9 ml. of concentrated hydrochloric acid and promptly neutralized with sodium hydrogen carbonate. The yield of 5-fluorouracil is calculated to be 89% from the ultraviolet absorption data of the reaction mixture.
Ultraviolet absorption spectrum:

$\lambda_{max}^{pH\ 1.0}$ 267 nm; $\lambda_{max}^{pH\ 7.0}$ 267 nm.

The reaction mixture is made acidic with 1 ml. of concentrated hydrochloric acid and passed through a column of activated carbon. The column is washed with water until the washings has become only weakly acidic (pH 5.0) and eluated with methanol. The eluate is concentrated to dryness under reduced pressure to give 47.8 mg. of 5-fluorouracil.

REFERENCE EXAMPLE 65

In 10 ml. of 1 N aqueous sodium hydroxide solution is dissolved 51.60 mg. of ethyl 5-fluoro-6-piperidino-1,2,3,4,5,6-hexahydro-2,4-dioxopyrimidine-5-carboxylate and the solution is allowed to stand at room temperature for 1 hour. It is then made acidic with 1.0 ml. of concentrated hydrochloric acid and promptly neutralized with sodium bicarbonate. Based on the ultraviolet absorption spectrum of the reaction mixture, the yield of 5-fluorouracil is 97%.

EXAMPLE 66

In 10 ml. of 1 N aqueous sodium hydroxide is dissolved 49.05 mg. of ethyl 6-n-butylamino-5-fluoro-1,2,3,4,5,6-hexahydro-2,4-dioxopyrimidine-5-carboxylate and the solution is allowed to stand at room temperature for 1 hour. The reaction mixture is made acidic with 1.0 ml. of concentrated hydrochloric acid and promptly neutralized with sodium bicarbonate. Based on the ultraviolet absorption spectrum of the reaction mixture, the yield of 5-fluorouracil is 76%.

EXAMPLE 67

A solution of 10.30 g. (50 mmoles) of methyl-5-fluoro-6-hydroxy-1,2,3,4,5,6-hexahydro-2,4-dioxopyrimidine-5-carboxylate, 4.6 g. of ethanol, 0.3 g. of methanesulfonic acid and 50 ml. of dimethoxyethane is heated under reflux for 3 hours. The reaction mixture is concentrated to dryness under reduced pressure. The concentrate is subjected to column chromatography on silica gel (solvent: acetone-chloroform=1:4(V/V)) to recover 8.0 g. of methyl 5-fluoro-6-ethoxy-1,2,3,4,5,6-hexahydro-2,4-dioxopyrimidine-5-carboxylate.

Melting Point: 185°–187° C. (Recrystallized from acetone-chloroform-hexane).

NMR spectrum (DMSO-$d_6$) δ: 1.10(3H, t, J=7$H_Z$), 3.3–4.0(2H, m), 3.78(3H, s), 4.82(1H, d×d, after addition of deuterium oxide, d, J=2$H_Z$), 8.93(1H, broad), 11.07(1H, broad).

Elemental analysis, for $C_8H_{11}FN_2O_5$: Calcd.: C, 41.03; H, 4.73; N, 11.96. Found: C, 40.75; H, 4.55; N, 11.68.

EXAMPLE 68

A solution of 17.6 g. (80 mmoles) of ethyl 5-fluoro-6-hydroxy-1,2,3,4,5,6-hexahydro-2,4-dioxopyrimidine-5-carboxylate, 4.8 g. of methanol, methanesulfonic acid and 100 ml. of 1,2-dimethoxyethane is heated under reflux for 3 hours. The reaction mixture is purified as in Example 67 to obtain 15.6 g. of ethyl 5-fluoro-6-methoxy-1,2,3,4,5,6-hexahydro-2,4-dioxopyrimidine-5-carboxylate.

Melting Point: 135°–137° C. (Recrystallized from acetone-chloroform-hexane).

NMR spectrum (DMSO-$d_6$) δ: 1.18(3H, t, J=7H$_Z$), 3.30(3H, s), 4.25(2H, q, J=7H$_Z$), 4.70(1H, d×d, after addition of deuterium oxide, d, J=2H$_Z$), 8.93(1H, broad), 11.02(1H, broad).

Elemental analysis, for $C_8H_{11}FN_2O_5$: Calcd.: C, 41.03; H, 4.73; N, 11.96. Found: C, 41.06; H, 4.58; N, 11.95.

EXAMPLE 69

2.35 g. of acetic anhydride, 2.05 g. of pyridine and 10 ml. of acetone are added to 4.40 g. (20 mmoles) of ethyl 5-fluoro-6-hydroxy-1,2,3,4,5,6-hexahydro-2,4-dioxopyrimidine-5-carboxylate. The mixture is allowed to stand overnight at room temperature and, then, following the addition of 10 ml. of isopropanol and 10 ml. of pyridine, heated under reflux for an hour. After distilling off the volatiles, the residue is purified as in Example 67 to obtain 3.7 g. of ethyl 5-fluoro-6-isopropoxy-1,2,3,4,5,6-hexahydro-2,4-dioxopyrimidine-5-carboxylate.

Melting Point: 216°–218° C. (Recrystallized from acetone-chloroform-hexane).

NMR spectrum (DMSO-$d_6$) δ: 1.07(6H, d, J=6H$_Z$), 1.16(3H, t, J=7H$_Z$), 3.82(1H, q, J=6H$_Z$), 4.25(2H, q, J=7H$_Z$), 4.83(1H, d×d, after addition of deuterium oxide d, J=2H$_Z$), 8.83(1H, broad), 11.00(1H, broad).

Elemental analysis, for $C_{10}H_{15}FN_2O_5$: Calcd.: C, 45.80; H, 5.77; N, 10.68. Found: C, 45.79; H, 5.74; N, 10.72.

EXAMPLE 70

A solution of 6.18 g. (30 mmoles) of methyl 5-fluoro-6-hydroxy-1,2,3,4,5,6-hexahydro-2,4-dioxopyrimidine-5-carboxylate, 2.96 g. of butyl alcohol, a catalytic amount of methanesulfonic acid and 40 ml. of 1,2-dimethoxyethane is heated under reflux for 1.5 hours. The reaction mixture is purified as in Example 67 to obtain 4.86 g. of methyl 5-fluoro-6-butoxy-1,2,3,4,5,6-hexahydro-2,4-dioxopyrimidine-5-carboxylate.

Melting Point: 140°–141° C. (Recrystallized from acetone-chloroform-hexane).

NMR spectrum (DMSO-$d_6$) δ: 0.6–1.8(7H, m), 3.56(2H, m), 3.89(3H, s), 4.82 (1H, d×d, after addition of deuterium oxide, d, J=2H$_Z$), 8.80(1H, broad), 10.97(1H, broad).

Elemental analysis, for $C_{10}H_{15}FN_2O_5$: Calcd.: C, 45.80; H, 5.77; N, 10.68. Found: C, 45.83; H, 5.59; N, 10.57.

EXAMPLE 71

In 50 ml. of acetone is dissolved 9.90 g. of ethyl 5-fluoro-6-hydroxy-1,2,3,4,5,6-hexahydro-2,4-dioxopyrimidine-5-carboxylate and, while the solution is stirred, 5.2 ml. of acetic anhydride and 9.0 ml. of pyridine are added and the mixture is allowed to stand overnight and, then, following the addition of 10 ml. of butanol, distilled under atmospheric pressure to remove acetone from the reaction mixture. There is obtained a pale yellow product which is dissolved in benzene and subjected to column chromatography on silica gel (150 g., solvent: chloroform-benzen=6:1 (V/V)) to recover a white solid from the fractions rich in the desired compound. The solid is recrystallized from acetone-chloroform-hexane to give 4.88 g. of ethyl 5-fluoro-6-butoxy-1,2,3,4,5,6-hexahydro-2,4-dioxopyrimidine-5-carboxylate as colorless needles.

Melting Point: 141°–142° C.

NMR spectrum (DMSO-$d_6$) δ: 0.87(3H, m), 1.22(3H, t, J=7H$_Z$), 1.45(4H, m), 3.60 (2H, m), 4.30(2H, q, J=7H$_Z$), 4.78(1H, d×d, $J_{HF}$=2H$_Z$, J=5H$_Z$, after addition of deuterium oxide, d, $J_{HF}$=2H$_Z$), 8.87(1H, broad), 10.98(1H, broad).

Elemental analysis, for $C_{11}H_{17}FN_2O_5$: Calcd.: C, 47.82; H, 6.20; N, 10.14. Found: C, 47.52; H, 6.22; N, 10.11.

EXAMPLE 72

A solution of 8.80 g. (40 mmoles) of ethyl 5-fluoro-6-hydroxy-1,2,3,4,5,6-hexahydro-2,4-dioxopyrimidine-5-carboxylate, 4.44 g. of isobutyl alcohol, 0.3 g. of methanesulfonic acid and 20 ml. of 1,2-dimethoxyethane is heated under reflux for 1.5 hours.

The reaction mixture is then purified as in Example 67 to give 6.44 g. of ethyl 5-fluoro-6-isobutoxy-1,2,3,4,5,6-hexahydro-2,4-dioxopyrimidine-5-carboxylate.

Melting Point: 187°–188° C. (Recrystallized from acetone-chloroform-hexane).

NMR spectrum (DMSO-$d_6$) δ: 0.78(6H, d, J=7H$_Z$), 1.15(3H, t, J=7H$_Z$), 1.4–2.0 (1H, m), 3.30(2H, d, J=7H$_Z$), 4.25(2H, q, J=7H$_Z$), 4.77(1H, d×d, after addition of deuterium oxide, d, J=2H$_Z$), 8.88(1H, broad), 11.00(1H, broad).

Elemental analysis, for $C_{11}H_{17}FN_2O_5$: Calcd.: C, 47.82; H, 6.20; N, 10.14. Found: C, 47.53; H, 6.20; N, 10.04.

EXAMPLE 73

A solution of 8.80 g. (40 mmoles) of ethyl 5-fluoro-6-hydroxy-1,2,3,4,5,6-hexahydro-2,4-dioxopyrimidine-5-carboxylate, 4.44 g. of sec-butyl alcohol, 0.3 g. of methanesulfonic acid and 20 ml. of 1,2-dimethoxyethane is heated under reflux for 2.5 hours. The reaction mixture is then purified as in Example 67 to give 5.58 g. of ethyl 5-fluoro-6-sec-butoxy-1,2,3,4,5,6-hexahydro-2,4-dioxopyrimidine-5-carboxylate.

Melting Point: 192°–194° C. (Recrystallized from acetone-chloroform-hexane).

NMR spectrum (DMSO-$d_6$) δ: 0.5–1.6(11H, m), 3.35–3.90(1H, m), 4.25(2H, q, J=7H$_Z$), 4.82(1H, d×d, after addition of deuterium oxide, d, J=2H$_Z$), 8.83(1H, broad), 11.00(1H, broad)

Elemental analysis, for $C_{11}H_{17}FN_2O_5$: Calcd.: C, 47.82; H, 6.20; N, 10.14. Found: C, 47.88; H, 6.30; N, 10.19.

EXAMPLE 74

In a solution of 4.40 g. (20 mmoles) of ethyl 5-fluoro-6-hydroxy-1,2,3,4,5,6-hexahydro-2,4-dioxopyrimidine-5-carboxylate, 2.70 g. of benzyl alcohol and 30 ml. of 1,2-dimethoxyethane, dry hydrogen chloride gas is introduced until about 3.4 g of hydrogen chloride is absorbed. The mixture is allowed to stand at room temperature overnight and, then, volatiles are distilled off under reduced pressure. The residue is purified as in Example 67 to obtain 3.20 g. of ethyl 5-fluoro-6-benzyloxy-1,2,3,4,5,6-hexahydro-2,4-dioxopyrimidine-5-carboxylate.

Melting Point: 132°–133° C. (Recrystallized from acetone-chloroform-hexane).

NMR spectrum (DMSO-d$_6$) δ: 1.18(3H, t, J=7H$_Z$), 4.26(2H, q, J=7H$_Z$), 4.65(2H, broad s), 4.97(1H, d×d, after addition of deuterium oxide, d, J=2H$_Z$), 7.33(5H, broad s), 9.05(1H, broad), 11.10(1H, broad).

Elemental analysis, for C$_{14}$H$_{15}$FN$_2$O$_5$: Calcd.: C, 54.19; H, 4.87; N, 9.03. Found: C, 54.19; H, 4.84; N, 9.08.

EXAMPLE 75

2.35 g. of acetic anhydride, 3 g. of pyridine and 10 ml. of acetone are added to 4.40 g. (20 mmoles) of ethyl 5-fluoro-6-hydroxy-1,2,3,4,5,6-hexahydro-2,4-dioxopyrimidine-5-carboxylate and the mixture is allowed to stand at room temperature overnight. Volatiles are evaporated and to the residue are added 2.82 g. of phenol, 20 ml. of pyridine and 10 ml. of 1,2-dimethoxyethane. The mixture is heated at 90° C. for one hour, then volatiles are distilled off from the mixture under reduced pressure and the residue is purified as in Example 67 to obtain 2.0 g. of ethyl 5-fluoro-6-phenoxy-1,2,3,4,5,6-hexahydro-2,4-dioxopyrimidine-5-carboxylate.

Melting Point: 164°–167° C. (Recrystallized from acetone-chloroform-hexane).

NMR spectrum (DMSO-d$_6$) δ: 1.21(3H, t, J=7H$_Z$), 4.28(2H, q, J=7H$_Z$), 5.74(1H, d×d, after addition of deuterium oxide, d, J=2H$_Z$), 6.8–7.5(5H, m), 9.30(1H, broad), 11.33(1H, broad)

Elemental analysis, for C$_{13}$H$_{13}$FN$_2$O$_5$: Calcd.: C, 52.71; H, 4.42; N, 9.46. Found: C, 52.14; H, 4.30; N, 9.87.

EXAMPLE 76

A solution of 8.24 g. (40 mmoles) of methyl 5-fluoro-6-hydroxy-1,2,3,4,5,6-hexahydro-2,4-dioxopyrimidine-5-carboxylate, 4.5 g. of butylmercaptan, a catalytic amount of methanesulfonic acid and 25 ml. of 1,2-dimethoxy-ethane is heated under reflux for 3 hours. The reaction mixture is purified as in Example 67 to obtain 8.3 g. of methyl 5-fluoro-6-butylthio-1,2,3,4,5,6-hexahydro-2,4-dioxopyrimidine-5-carboxylate.

Melting Point: 123°–125° C. (Recrystallized from acetone-chloroform-hexane).

NMR spectrum (DMSO-d$_6$) δ: 0.80(3H, t, J=7H$_Z$), 1.0–1.8(4H, m), 2.66(2H, t, J=7H$_Z$), 3.76(3H, s), 5.08(1H, d×d, after addition of deuterium oxide, d, J=7.5H$_Z$), 8.75(1H, broad), 11.13(1H, broad).

Elemental analysis, for C$_{10}$H$_{15}$FN$_2$O$_4$S: Calcd.: C, 43.16; H, 5.43; N, 10.07. Found: C, 43.21; H, 5.24; N, 10.02.

EXAMPLE 77

2.35 g. of acetic anhydride, 2.05 g. of pyridine and 10 ml. of acetone are added to 4.40 g. (20 mmoles) of ethyl 5-fluoro-6-hydroxy-1,2,3,4,5,6-hexahydro-2,4-dioxopyrimidine-5-carboxylate.

The mixture is allowed to stand at room temperature overnight and, then, following the addition of 3.3 g. of thiophenol and 5 g. of pyridine, reacted at 60° C. for 1.5 hours. Volatiles are distilled off under reduced pressure and the residue is purified as in Example 67 to obtain 4.82 g. of ethyl 5-fluoro-6-phenylthio-1,2,3,4,5,6-hexahydro-2,4-dioxopyrimidine-5-carboxylate.

Melting Point: 164°–166.5° C. (Recrystallized from acetone-chloroform-hexane).

NMR spectrum (DMSO-d$_6$) δ: 1.18(3H, t, J=7H$_Z$), 4.28(2H, q, J=7H$_Z$), 5.37(1H, t, after addition of deuterium oxide, d, J$_{HF}$=3H$_Z$), 7.40(5H, broad), 8.87(1H, broad), 11.13(1H, broad).

Elemental analysis, for C$_{13}$H$_{13}$FN$_2$O$_4$S: Calcd.: C, 49.99; H, 4.20; N, 8.97. Found: C, 49.55; H, 3.98; N, 9.09.

EXAMPLE 78

In 400 ml. of acetic acid is suspended 2.05 g. of 1,2,3,4-tetrahydro-2,4-dioxopyrimidine-5-carbonitrile and, with vigorous stirring a mixed gas of fluorine and nitrogen (15:85 (V/V)) is introduced. When about 1.5 molar equivalents to fluorine to the substrate has been introduced, the reaction mixture is evapolated to dryness. Ethanol (70 ml.) is added to the residue and the mixture is heated under reflux for 2 hours and, then, evapolated to dryness again. The resultant syrup is subjected to column chromatography on silica gel (solvent:benzene-acetone=4:1(V/V)) to recover 1.54 g. of 5-fluoro-6-ethoxy-1,2,3,4,5,6-hexahydro-2,4-dioxopyrimidine-5-carbonitrile as white crystals.

Melting Point: 195°–196° C.

NMR spectrum (DMSO-d$_6$) δ: 1.07(3H, t, J=7H$_Z$), 3.64(2H, q×d, J=7H$_Z$ and J=2H$_Z$), 5.42(1H, d×d, J=4H$_Z$ and J=2H$_Z$), 9.38(1H, broad), 11.59(1H, broad).

Elemental analysis, for C$_7$H$_8$FN$_3$O$_3$: Calcd.: C, 41.80; H, 4.01; N, 20.89. Found: C, 41.44; H, 3.95; N, 20.70.

EXAMPLE 79

In 200 ml. of dry dioxane is dissolved 10.0 g. of ethyl 5-fluoro-6-hydroxy-2,4-dioxo-1,2,3,4,5,6-hexahydropyrimidine-5-carboxylate. To this, are added 11.8 g. of octyl alcohol, 0.3 g. of p-toluenesulfonic acid and 3.0 g. of anhydrous magnesium sulfate. The mixture is heated under reflux with stirring. The reaction mixture is evaporated to dryness under reduced pressure. To the residue is added hexane and the resultant precipitate is recovered by filtration. The filtrate is chromatographed on a column of silica gel (solvent:chroloform-acetone=95:5(V/V)) to give 8.4 g. of white chrystalline powder. The powder is recrystallized twice from ethyl acetatehexane to obtain 6.37 g. of ethyl 5-fluoro-6-octyloxy-2,4-dioxo-1,2,3,4,5,6-hexahydropyrimidine-5-carboxylate as a white powder.

Melting Point: 123°–124° C.

NMR spectrum (CDCl$_3$) δ: 0.88–1.17(3H, m), 1.20–1.98(15H, m), 3.60–3.93(2H, m), 4.48(2H, q, J=7H$_Z$), 5.11(1H, d×d, J=5H$_Z$, J=2H$_Z$, after addition of deuterium oxide, d, J=2H$_Z$), 7.82 (1H, broad), 9.38(1H, broad).

Elemental analysis, for C$_{15}$H$_{25}$FN$_2$O$_5$: Calcd.: C, 54.21; H, 7.58; N, 8.43. Found: C, 54.32; H, 7.73; N, 8.39.

EXAMPLE 80

A mixture of 72.8 g. of ethyl 5-fluoro-6-hydroxy-1,2,3,4,5,6-hexahydro-2,4-dioxopyrimidine-5-carboxylate, 52.0 g. of octyl alcohol, 700 ml. of toluene and 7.0 g. of methanesulfonic acid is heated under reflux on an oil bath maintained at 140° C., while the water formed by the reaction is removed as an azeotrope from the reaction mixture. The heating is stopped after an hour and the reactant is allowed to cool and, then, some precipitates are filtered off. The filtrate is chromatographed on a column of silica gel (400 g., solvent:-chloroform-methanol=100:1(V/V)). From the fractions rich in the desired compound is obtained, after evaporation of the solvent, 96.8 g. of crude ethyl 5-fluoro-6-octyloxy-1,2,3,4,5,6-hexahydro-2,4-dioxopyrimidine-5-carboxylate (a mixture of cis- and trans-compound) as a white solid. The solid is recrystallized twice from ethanol-hexane to obtain 40.2 g. of ethyl 5-fluoro-t-6-octyloxy-1,2,3,4,5,6-hexahydro-2,4-dioxopyrimidine-r-5-carboxylate as colorless needles. Based on thin-layer chromatographic and NMR data, this product is identified completely with a sample synthesized by another method.

Melting Point: 126°–127° C.

NMR spectrum (CDCl$_3$) δ: 0.90(3H, m), 1.28(15H, broad), 3.72(2H, m), 4.38(2H, q, J=7H$_Z$), 5.12(1H, broad, after addition of deuterium oxide, d, J$_{HF}$=2H$_Z$), 8.22(1H, broad), 9.90(1H, broad).

Elemental analysis, for C$_{15}$H$_{25}$FN$_2$O$_5$: Calcd.: C, 54.20; H, 7.58; N, 8.43. Found: C, 54.40; H, 7.79; N, 8.32.

The mother liquor of the recrystallization is chromatographed on a column of silica gel (300 g., solvent:- chloroform-benzene=4:1, then=7:1 (V/V), and then chloroform-methanol=20;1(V/V)) to obtain fractions of r-5-t-6 compound (10.7 g.), a mixture (4.3 g.) of r-5-t-6 and r-5-c-6 compounds and r-5-c-6 compound (3.0 g.). The product from the last fraction is recrystallized to obtain 0.5 g. of ethyl 5-fluoro-c-6-octyloxy-1,2,3,4,5,6-hexahydro-2,4-dioxopyrimidin-r-5-carboxylate as a colorless prisms.

Melting Point: 148°–149° C.

NMR spectrum (CDCl$_3$) δ: 0.90(3H, m), 1.28(15H, broad), 3.73(2H, m), 4.42(2H, q, J=7H$_Z$), 5.13(1H, broad d, J=11H$_Z$, after addition of deuterium oxide, d, J$_{HF}$=11H$_Z$), 7.63(1H, broad), 9.75(1H, broad).

Elemental analysis, for C$_{15}$H$_{25}$FN$_2$O$_5$: Calcd.: C, 54.20; H, 7.58; N, 8.43. Found: C, 54.43; H, 8.19; N, 8.45.

EXAMPLE 81

11.2 g. of ethyl 5-fluoro-6-hydroxy-1,2,3,4,5,6-hexahydro-2,4-dioxopyrimidine-5-carboxylate, 4.2 g. of butanol, 2.7 g. of methanesulfonic acid, 100 ml. of dioxane and 5.0 g. of molecular sieves (3A) are mixed and the mixture is heated with stirring on an oil bath maintained at a temperature between 60° and 70° C. for 5.5 hours. The reaction mixture is allowed to cool and, then, insoluble materials are filtered off. The filtrate is concentrated under reduced pressure and the yellow oily residue is dissolved in 400 ml. of chloroform. The solution is washed by an aqueous solution of sodium bicarbonate to remove the acid. The chloroform solution is dried over anhydrous magnesium sulfate and concentrated under reduced pressure to obtain 10.1 g. of a white solid. From the NMR spectrum and the thin-layer silica gel chromatographic behavior the white solid is identified as ethyl 6-butoxy-5-fluoro-1,2,3,4,5,6-hexahydro-2,4-dioxopyrimidine-5-carboxylate.

EXAMPLE 82

In 40 ml. of acetone is dissolved 4.4 g. of ethyl 5-fluoro-6-hydroxy-1,2,3,4,5,6-hexahydro-2,4-dioxopyrimidin-5-carboxylate. To this, are added 2.4 ml. of acetic anhydride and 2.0 ml. of pyridine and the solution is allowed to stand at room temperature for 21.5 hours. To the solution thus obtained is added 3.5 ml. of allyl amine, whereby a reaction takes place with evolution of heat to yield a brown-colored solution. After an hour's standing at room temperature, the reaction mixdure is concentrated to dryness under reduced pressure to obtain a brown solid which is suspended in chloroform and filtered to obtain a white solid. The solid is recrystallized from acetone-hexane to obtain 2.2 g. of ethyl 6-allylamino-5-fluoro-1,2,3,4,5,6-hexahydro-2,4-dioxopyrimidine-5-carboxylate as colorless needles.

NMR spectrum (DMSO-d$_6$) δ: 1.23(3H, t, J=7H$_Z$), 2.63(1H, m), 3.30(2H, m), 4.27(2H, q, J=7H$_Z$), 4.47(1H, m, after addition of deuterium oxide, d, J$_{HF}$=8H$_Z$), 4.9–5.4(2H, m), 5,6–6.2(1H, m), 8.35(1H, broad), 10.88(1H, m).

EXAMPLE 83

In a pressure-resistant glass tubular reactor of 100 ml. capacity, methyl 1,2,3,4-tetrahydro-2,4-dioxopyrimidine-5-carboxylate (510 mg., 3.0 mmoles) is suspended in 20 ml. of water and the suspension is frozen in a dry ice-ethanol bath. Onto the frozen solid is poured 20 ml. of fluorotrichloromethane and, under cooling in the same cooling bath, trifluoromethyl hypofluorite (ca. 400 mg.) is dissolved in it. After the reactor is closed tightly, the cooling bath is taken away to let the mixture warm up to room temperature. The starting material promptly reacts and dissolved in the water. The reaction mixture is stirred overnight, whereby no solid matter remains undissolved. The excess trifluoromethyl hypofluorite is removed by passing nitrogen gas through the solution, and anhydrous sodium acetate (400 mg.) is added to the solution. The solution is concentrated to dryness under reduced pressure and the residue is washed with acetone. The acetone solution is concentrated under reduced pressure to give 700 mg. of methyl 5-fluoro-6-hydroxy-1,2,3,4,5,6-hexahydro-2,4-dioxopyrimidine-5-carboxylate as a yellow vitreous solid. The product is identified with the objective compound by the nuclear magnetic resonance spectrum. Its thin-layer chromatogram on silica gel (chloroform-methanol=6:1 V/V) give a single spot.

NMR spectrum (DMSO-d$_6$) δ: 3.80(3H, s), 4.90(1H, m, after addition of deuterium oxide, d, J$_{HF}$=4H$_Z$), 7.13(1H, d, J=5H$_Z$), 8.53(1H, broad), 10.85(1H, broad).

EXAMPLE 84

In a pressure-resistant glass tubular reactor of 50 ml. capacity, methyl 1,2,3,4-tetrahydro-2,4-dioxopymidine-5-carboxylate (510 mg., 3.0 mmoles) is suspended in 20 ml. of water and the suspension is frozen in a dry ice-ethanol bath. To the frozen solid is added 20 ml. of trifluoroacetic acid, followed by dissolution of trifluoromethyl hypofluorite (about 290 mg.). The reactor is closed tightly and the suspension is allowed to warm up spontaneously to room temperature. With the rising temperature, the reaction proceeds to give a homogeneous solution. This reaction mixture is stirred overnight. The excess trifluoromethyl hypofluorite is removed by passing nitrogen gas through the solution, and then following the addition of sodium bicarbonate (540 mg.), the solvent is removed under reduced pressure, which leaves a colorless syrup. To this syrup is added 30 ml. of acetone and the insolubles are filtered off. The acetone solution is concentrated under reduced pressure to recover 1.15 g. of a pale yellow syrup. By thin-layer chromatography on silica gel and nuclear magentic resonance spectrum, this product is identified with methyl 5-fluoro-6-hydroxy-1,2,3,4,5,6-hexahydro-2,4-dioxopyrimidine-5-carboxylate.

EXAMPLE 85

In a pressure-resistant glass tubular reactor of 100 ml. capacity, 1,2,3,4-tetrahydro-2,4-dioxopyrimidine-5-carbonitrile (1.10 g., 8.0 mmoles) is suspended in 35 ml. of water and the suspension is frozen in a dry ice-ethanol. Onto this frozed solid is poured 35 ml. of fluorotrichloromethane and, under cooling in the same cooling bath, trifluoromethyl hypofluorite (about 1.2 g.) is dissolved in it. After the reactor is closed tightly, the contents are stirred at room temperature for 40 hours, whereby no starting material remains undissolved. The excess trifluoromethyl hypofluorite is removed by passing nitrogen gas through the solution and, after addition of sodium bicarbonate (690 mg.), the solvent is removed under reduced pressure. To the resultant brown-colored syrup is added acetone and the insolubles are filtered off. The acetone solution is concentrated under reduced pressure to recover 1.74 g. of a brown-colored vitreous solid. The thin-layer chromatogram of this solid on silica gel (chloroform-methanol=6:1 V/V) shows two distinct spots and, by the nuclear magnetic resonance spectrum thereof, it was found to be an approximately 1:1 mixture of 5-fluoro-6-hydroxy-1,2,3,4,5,6-hexahydro-2,4-dioxopyrimidine-5-carbonitrile and 3,5-difluoro-6-hydroxy-1,2,3,4,5,6-hexahydro-2,4-dioxopyrimidine-5-carbonitrile.

NMR spectrum (DMSO-$d_6$) δ: 5.33(1H, m, after addition of deuterium oxide, d, $J_{HF}=3H_Z$), 7.7–8.2(1H, broad), 9.00(1H, broad), 10.3–11.0($\frac{1}{2}$H, broad, assignable to $N^3$—H).

EXAMPLE 86

A cylindrical reactor of Pyrex glass, 40 mm in diam. and 300 mm. high, equipped with a thermometer, a Teflon gas inlet pipe and a gas outlet pipe leading to a trap containing potassium iodide solution is charged with 3.25 g. (25 mmoles) of methyl 1,2,3,4-tetrahydro-2,4-dioxopyrimidine-5-carboxylate and 250 ml. of water and under cooling with cold water, the contents are stirred magnetically. To this is introduced a current of fluorine gas previously diluted with nitrogen to a fluorine-to-nitrogen ratio of 1:9 (V/V) at a flow rate of about 100 ml./min. over a period of about 1 hour and a half until the solid starting material has completely dissolved. Approximately 1.5 molar equivalents of fluorine gas has been consumed. After introducing nitrogen gas into the reaction system for a while, the reaction mixture is concentrated under reduced pressure and further evaporated in vacuo. By the above procedure was obtained 4.32 g. of crude methyl 5-fluoro-6-hydroxy-1,2,3,4,5,6-hexahydro-2,4-dioxopyrimidine-5-carboxylate as a white vitreous solid.

EXAMPLE 87

In a pressure-resistant glass tubular reactor of 300 ml. capacity, 25 ml. of methanol is mixed with 50 ml. of fluorotrichloromethane and the mixture is well cooled in a dry ice-ethanol bath. In this mixture is dissolved trifluoromethyl hypofluorite (about 1.1 g.) and, then, methyl 1,2,3,4-tetrahydro-2,4-dioxopyrimidine-5-carboxylate (1.36 g., 8.0 mmoles) is suspended, followed by the addition of 80 ml. of methanol previously cooled in a dry ice-ethanol bath. After the reactor is tightly closed, the reaction mixture is allowed to warm up spontaneously to room temperature under stirring. With the rising temperature, the starting material dissolves swiftly to yield a homogeneous solution. The solution is stirred overnight. Next, nitrogen gas is bubbled into the solution to remove the excess trifluoromethyl hypofluorite and, then, the reaction mixture is evaporated under reduced pressure to give a white solid. This solid is chromatographed on a column of silica gel (solvent:chloroform containing 1 to 10 V/V % of methanol) to isolate 1.52 g. of methyl 5-fluoro-6-methoxy-1,2,3,4,5,6-hexahydro-2,4-dioxopyrimidine-5-carboxylate and 0.31 g. of the unreacted starting material. The desired product is recrystallized from acetone and hexane to give 1.26 g. of pure compound as colorless flakes.

Melting Point: 165°–166° C.

NMR spectrum (DMSO-$d_6$) δ: 3.38(3H, s), 3.85(3H, s), 4.77(1H, d×d, $J_{HF}=2H_Z$, J=5$H_Z$, after addition of deuterium oxide, d, $J_{HF}=2H_Z$), 8.77(1H, broad), 10.92(1H, broad).

Elemental analysis, for $C_7H_9FN_2O_5$: Calcd.: C, 38.19; H, 4.12; N, 12.76; F, 8.63. Found: C, 38.49; H, 4.06; N, 12.50; F, 7.92.

EXAMPLE 88

In 25 ml. of 1 N hydrochloric acid, methyl 5-fluoro-6-hydroxy-1,2,3,4,5,6-hexahydro-2,4-dioxopyrimidine-5-carboxylate (1.20 g., 5.8 mmoles) is heated under reflux for 1 hour. The reaction mixture is treated with activated carbon and evaporated under reduced pressure, whereupon a brown-colored solid is obtained. This solid product is washed with acetone and dried to recover 695 mg. of yellow prisms. The crystals are further purified by dissolving them in a mixture of 50 ml. water and 1 ml. 1 N hydrochloric acid and the solution passed through a column of activated carbon. The column is washed well with water and the adsorbed organic material is eluted with 350 ml. of methanol-water-benzene=25:6:3. The eluate is evaporated under reduced pressure to give 490 mg. of a white powder. In a thin-layer chromatography on silica gel (chloroform-methanol=6:1), this powder agrees with an authentic sample of 5-fluorouracil. Based on the following physical constants, this product is further identified with 5-fluorouracil.

$\lambda_{max}^{pH\ 7.0}$ 267 nm.

NMR spectrum (DMSO-$d_6$) δ: 7.72(1H, d×d, J=6$H_Z$, after addition of deuterium oxide, d, $J_{HF}=6H_Z$), 10.82(1H, broad), 11.47(1H, broad).

EXAMPLE 89

In 1.5 N hydrochloric acid, methyl 5-fluoro-6-methoxy-1,2,3,4,5,6-hexahydro-2,4-dioxopyrimidine-5-carboxylate (0.65 g., 2.7 mmoles) is heated under reflux for 2.5 hours. The reaction mixture is treated with decolorizing carbon and evaporated under reduced pressure to give colorless prisms. Following addition of 10 ml. of methanol and a small amount of water to the crystals, the mixture is allowed to stand in a refrigerator overnight. The resultant crystals are collected by filtration, washed with a small amount of methanol and dried to give 0.17 g. of colorless prisms. The mother liquid is concentrated under reduced pressure to recover 200 mg. of a pale yellow solid. Based on the thin-layer chromatographic behavior and the following physical constants, both the crystals and the pale-yellow solid are identified with 5-fluorouracil.

UV spectrum: $\lambda_{max}^{pH\ 1.0}$ 267 nm, $\lambda_{max}^{pH\ 7.0}$ 267 nm.

NMR spectrum (DMSO-$d_6$) δ: 7.70(1H, d×d, J=6$H_Z$ & 6$H_Z$, after addition of deuterium oxide, d, $J_{HF}=6H_Z$), 10.68(1H, broad), 11.43(1H, broad).

EXAMPLE 90

In 40 ml. of concentrated hydrochloric acid, 1.66 g. of a mixture of the 5-fluoro-6-hydroxy-1,2,3,4,5,6-hexahydro-2,4-dioxopyrimidine-5-carbonitrile and 3,5-difluoro-6-hydroxy-1,2,3,4,5,6-hexahydro-2,4-dioxopyrimidine-5-carbonitrile obtained in Example 85 is heated under reflux for 6.5 hours. The reaction mixture is adjusted to pH 2 by the addition of anhydrous potassium carbonate and desalted by means of a column of activated carbon. The organic material adsorbed is eluted with 500 ml. of mixture of methanol and benzene (4:1). The eluate is evaporated under reduced pressure to give 760 mg. of a white powder.

This product is identified with 5-fluorouracil based on its agreement with an authentic sample in a thin-layer chromatography (silica gel) as well as on the following physical constants.

UV spectrum: $\lambda_{max}^{pH\ 7.0}$ 267 nm.

NMR spectrum (DMSO-$d_6$) δ: 7.70(1H, d×d, $J=6H_Z$ & $6H_Z$, after addition of deuterium oxide, d, $J_{HF}=6H_Z$), 10.68(1H, broad), 11.47(1H, broad).

EXAMPLE 91

In a pressure-resistant glass tubular reactor, 1,2,3,4-tetrahydro-2,4-dioxopyrimidine-5-carboxamide (460 mg., 3 mmoles) is suspended in 20 ml. of water. The suspension is frozen in a dry ice-ethanol bath, followed by addition of 20 ml. of fluoro-trichloromethane. Under cooling in the same bath, trifluoromethyl hypofluorite (ca 990 mg.) is added. After the reactor is tightly closed, the contents are stirred at room temperature for 160 hours. The excess trifluoromethyl hypofluorite is removed by passing nitrogen gas through the solution, and, following addition of anhydrous sodium acetate (1.3 g.), the solvent is evaporated under reduced pressure. The resultant red solid is washed with a mixture of methanol and acetone (1/10 (V/V)) and the insolubles (a part of the starting material and some inorganic salt) are filtered off. The filtrate is concentrated under reduced pressure to yield 1.55 g. of a red syrup which is found by nuclear magnetic resonance spectrum to be 3,5-difluoro-6-hydroxy-1,2,3,4,5,6-hexahydro-2,4-dioxopyrimidine-5-carboxamide.

NMR spectrum (DMSO-$d_6$) δ: 4.93(1H, m, after addition of deuterium oxide, d, $J_{HF}=2.5H_Z$, —CF=C$\underline{H}$—), 8.35(1H, broad, $N^1$—$\underline{H}$)

No peak assignable to $N^3$-proton.

The above red syrup is refluxed in concentrated hydrochloric acid for 5 hours, then adjusted to pH 1 with a necessary amount of potassium carbonate. The reaction mixture is desalted by passing through a column of activated carbon. The organic material adsorbed on the carbon is eluted with a solvent mixture of 300 ml. methanol and 100 ml. benzene and the eluate is then evaporated under reduced pressure to yield 230 mg. of a white powder.

Based on its thin-layer chromatogram on silica gel and the following physical constants, this powder is identified with 5-fluorouracil.

UV spectrum: $\lambda_{max}^{pH\ 7.0}$ 267 nm.

NMR spectrum (DMSO-$d_6$) δ: 7.70(1H, d×d, $J=5H_Z$ & $J_{HF}=6H_Z$), 10.68(1H, broad), 11.47(1H, broad).

Melting Point: 282°–283° C. (colorless prisms, recrystallized from water).

Elemental analysis, for $C_4H_3FN_2O_2$: Calcd.: C, 36.93; H, 2.32; N, 21.54; F, 14.61. Found: C, 36.90; H, 2.24; N, 21.46; F, 14.37.

EXAMPLE 92

In 100 ml. of methanol is suspended methyl 1,2,3,4-tetrahydro-2,4-dioxopyrimidine-5-carboxylate (3.40 g., 20.0 mmoles) and, under vigorous stirring at room temperature, chlorine gas is bubbled into the suspension. The end point of the reaction is attained when the solid matter has completely dissolved. The reaction mixture is concentrated under reduced pressure to 1/10 of its initial volume, followed by the addition of 80 ml. of ethyl acetate. The resultant precipitate is recovered by filtration and recrystallized from acetone-hexane to give 3.55 g. of methyl 5-chloro-6-methoxy-1,2,3,4,5,6-hexahydro-2,4-dioxopyrimidine-5-carboxylate as colorless needles.

Melting Point: 164°–166° C.

NMR spectrum (DMSO-$d_6$) δ: 3.37(3H, s), 3.80(3H, s), 4.73(1H, d, $J=5H_Z$), 9.10(1H, broad), 10.95(1H, broad).

Elemental analysis, for $C_7H_9ClN_2O_5$ (mol. wt. 236.62): Calcd.: C, 35.53; H, 3.83; N, 11.84; Cl, 14.99. Found: C, 35.41; H, 3.88; N, 11.76; Cl, 15.22.

EXAMPLE 93

In 240 ml. of water is suspended methyl 1,2,3,4-tetrahydro-2,4-dioxopyrimidine-5-carboxylate (14.06 g., 83 mmoles) and, under intense stirring at room temperature, chlorine gas is bubbled into the suspension. The reaction is complete when the solid matter has dissolved. The reaction mixture is concentrated under reduced pressure to one-tenth of its initial volume to yield 14.82 g. of methyl 5-chloro-6-hydroxy-1,2,3,4,5,6-hexahydro-2,4-dioxopyrimidine-5-carboxylate as a yellow solid.

Melting Point: 179°–181° C. (colorless flakes, recrystallized from acetone-hexane).

NMR spectrum (DMSO-$d_6$) δ: 3.78(3H, s), 4.98(1H, d, $J=4H_Z$), 6.5(1H, broad), 8.57(1H, broad), 10.80(1H, broad).

Elemental analysis, for $C_6H_7ClN_2O_5$: Calcd.: C, 32.37; H, 3.17; N, 12.59, Cl, 15.93. Found: C, 32.34; H, 2.94; N, 12.56; Cl, 16.14.

EXAMPLE 94

In 60 ml. of water is suspended methyl 1,2,3,4-tetrahydro-2,4-dioxopyrimidine-5-carboxylate (2.55 g., 15.0 mmoles) and, under intense stirring at room temperature, chlorine gas is bubbled into the suspension. The reaction is complete when the solid has dissolved. Following addition of 10 ml. of concentrated hydrochloric acid, the reaction mixture is refluxed for 16 hours. It is then concentrated under reduced pressure to one-fifth of its initial volume to give 1.39 g. of 5-chlorouracil as pale yellow needles.

Melting Point: above 300° C.

UV spectrum: $\lambda_{max}^{pH\ 1.0}$ 274 nm, $\lambda_{max}^{pH\ 7.0}$ 275 nm.

NMR spectrum (DMSO-$d_6$) δ: 7.75(1H, d, $J=6H_Z$), 11.17(1H, broad), 11.48(1H, broad).

Elemental analysis, for $C_4H_3ClN_2O_2$: Calcd.: C, 32.78; H, 2.06; N, 19.12; Cl, 24.20. Found: C, 32.54; H, 1.97; N, 19.02; Cl, 24.30.

EXAMPLE 95

In 15 ml. of concentrated hydrochloric acid, 345 mg. of methyl 5-chloro-6-hydroxy-1,2,3,4,5,6-hexahydro- 2,4-dioxopyrimidine-5-carboxylate is heated under reflux for 15 hours. The reaction mixture is cooled with ice, whereupon 92 mg. of 5-chlorouracil is obtained as colorless prisms.

UV spectrum: $\lambda_{max}^{pH\ 1.0}$ 274 nm, $\lambda_{max}^{pH\ 7.0}$ 275 nm.

NMR spectrum (DMSO-$d_6$) δ: 7.75(1H, d, J=6Hz), 11.17(1H, m), 11.48(1H, br.).

EXAMPLE 96

3.40 g. (20 mmoles) of methyl 1,2,3,4-tetrahydro-2,4-dioxopyrimidine-5-carboxylate is boiled with a mixture of 12 ml. of hexamethyldisilazane and 0.3 ml. of trimethylsilyl chloride on an oil bath at 150°–165° C. for 2 hours. Then, the excess hexamethyldisilazane is distilled off under reduced pressure to obtain 6.60 g. of methyl 2,4-bis(trimethylsilyloxy)pyrimidine-5-carboxylate as an oily residue.

NMR spectrum (DMSO-$d_6$) δ: 0.30(18H, s), 3.73(3H, s), 8.78(1H, s).

The above bis-silyl derivative is cooled to −70° C., and a preprepared solution of 2-chlorotetrahydrofuran in dimethoxyethane (prepared by admixing 2.8 g. (40 mmoles) of 2,3-dihydrofuran with 20 ml. of dimethoxyethane containing 1.35 g. (37 mmoles) of dry hydrogen chloride and allowing the mixture to stand at −20° C. for 12 hours) is added. The resultant mixture is allowed to stand at room temperature overnight. The low-boiling fraction is distilled off under reduced pressure. To the residue, 50 ml. of a 10:1 (V/V) mixture of ether and methanol is added and the insolubles are recovered by filtration to obtain 3.93 g. of powder. The filtrate is concentrated under reduced pressure and, following addition of 10 ml. of ether, the insolubles are recovered by filtration to obtain a second crop (0.85 g.) of powder. The powders are combined and purified on a short column of silica gel (solvent:chloroform-acetone-methanol=50:45:5 (V/V)) to yield 4.63 g. of colorless powder. Based on thin-layer chromatographic (Rf), IR and NMR data, this product is identified with an authentic sample of methyl 1-(2-tetrahydrofuryl)-1,2,3,4-tetrahydro-2,4-dioxopyrimidine-5-carboxylate.

EXAMPLE 97

A mixture of 5.52 g. (30 mmoles) of ethyl 1,2,3,4-tetrahydro-2,4-dioxopyrimidine-5-carboxylate, 15 g. of 2,3-dihydrofuran and 15 ml. of pyridine is heated at 135° C. for 6 hours. The reaction mixture is concentrated to dryness under reduced pressure and, with the addition of 20 ml. of water, the pyridine is azeotropically removed. The residue is dissolved in 50 ml. of 50% ethanol and heated at 75° C. for 2 hours. The reaction mixture is concentrated to dryness under reduced pressure and the residue is stirred well with 40 ml. of chloroform. Then, 0.9 g. of insoluble ethyl 1,2,3,4-tetrahydro-2,4-dioxopyrimidine-5-carboxylate is recovered. The mother liquor is concentrated to dryness and the residue is recrystallized from 15 ml. of ethanol to give 3.1 g. (yield: 40.6%) of ethyl 1-(2-tetrahydrofuryl)-1,2,3,4-tetrahydro-2,4-dioxopyrimidine-5-carboxylate, melting point: 125° C.

Elemental analysis, for $C_{11}H_{14}N_2O_5$: Calcd.: C, 51.96; H, 5.55; N, 11.02. Found: C, 51.86; H, 5.54; N, 10.81.

NMR spectrum (DMSO-$d_6$) δ: 11.45(1H, broad, NH) 8.15(1H, s, H-6),

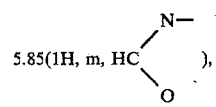
5.85(1H, m, HC⟨N—, O⟩),

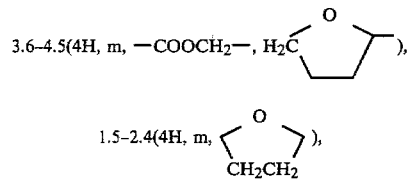
3.6–4.5(4H, m, —COOCH$_2$—, H$_2$C⟨O⟩),

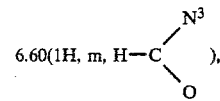
1.5–2.4(4H, m, ⟨O, CH$_2$CH$_2$⟩), 1.28(3H, t, —CH$_3$).

Thin-layer chromatography (silica gel; ethanol-chloroform=1:9): Rf=0.5.

EXAMPLE 98

In 14 ml. of pyridine are dissolved 3.4 g. (20.0 mmoles) of methyl 1,2,3,4-tetrahydro-2,4-dioxopyrimidine-5-carboxylate and 4.9 g. (70.0 mmoles) of 2,3-dihydrofuran and the solution is heated in a closed reaction vessel at 140° C. for 6 hours. The reaction mixture is then concentrated to dryness under reduced pressure and the residue is dissolved in 30 ml. of chloroform and applied to a column of 68 g. of silica gel. Elution is carried out with 250 ml. of chloroform and the eluate is concentrated to dryness under reduced pressure to give 0.8 g. (yield 12.9%) of methyl 1,3-bis(2-tetrahydrofuryl)-1,2,3,4-tetrahydro-2,4-dioxopyrimidine-5-carboxylate.

NMR (CDCl$_3$) δ: 8.25(1H, s, H-5)

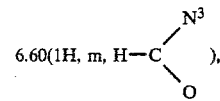
6.60(1H, m, H—C⟨N$^3$, O⟩),

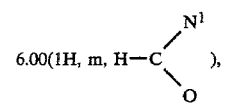
6.00(1H, m, H—C⟨N$^1$, O⟩),

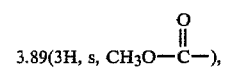
3.89(3H, s, CH$_3$O—C(=O)—),

Elemental analysis, for $C_{14}H_{18}N_2O_6$: Calcd.: C, 54.19; H, 5.85; N, 9.03. Found: C, 53.98; H, 5.97; N, 8.92.

The column used for the elution of said bisfuranidyl compound is further eluted with 350 ml. of CHCl$_3$-EtOH (97:3) and the eluate is concentrated to dryness under reduced pressure. The residue is recrystallized from 20 ml. of ethanol to give 2.04 g. of methyl 1-(2-tetrahydrofuryl)-1,2,3,4-tetrahydro-2,4-dioxopyrimidine-5-carboxylate as colorless needles. Yield 42.6%; melting point: 191° C. (decomp.).

NMR (DMSO-$d_6$) δ: 8.20(1H, s, H-5),

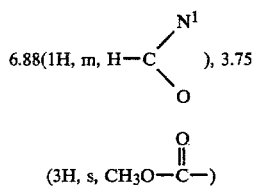
6.88(1H, m, H—C⟨N$^1$, O⟩), 3.75

(3H, s, CH$_3$O—C(=O)—)

Elemental analysis, for $C_{10}H_{12}N_2O_5$: Calcd.: C, 50.00; H, 5.04; N, 11.66. Found: C, 50.05; H, 5.35; N, 11.58.

EXAMPLE 99

In 6 ml. of 50% ethanol is dissolved 0.62 g. (2.0 mmoles) of the 1,3-bis-(2-tetrahydrofuryl)-1,2,3,4-tetrahydro-2,4-dioxopyrimidine-5-carboxylate obtained in Example 98 and the solution is heated at 70° C. for 1.5 hours. The reaction mixture is concentrated to dryness under reduced pressure and the residue is recrystallized from 3 ml. of ethanol to give 394 mg. of methyl 1-(2-tetrahydrofuryl)-1,2,3,4-tetrahydro-2,4-dioxopyrimidine-5-carboxylate as colorless needles. (yield 82.0%); melting point: 191° C. (decomp.).

This product is in agreement with the sample product according to Example 98, giving a single spot at Rf 0.58 in thin-layer chromatography [silica gel: $CHCl_3$-EtOH (9:1)].

EXAMPLE 100

In 200 ml. of glacial acetic acid is dissolved 1.38 g. of methyl 1-(2-tetrahydrofuryl)-1,2,3,4-tetrahydro-2,4-dioxopyrimidine-5-carboxylate and the fluorination is carried out at 18° C. to 24° C. using a gaseous mixture of fluorine (15 V/V %) and nitrogen. When the mixed gas equivalent to 2.2 moles of fluorine has been introduced, the absence of any residual starting material is confirmed by ultraviolet absorption spectrum. The solvent is then distilled off under reduced pressure to give a colorless syrup of methyl 6-acetoxy-5-fluoro-1-(2-tetrahydrofuryl)-1,2,3,4,5,6-hexahydro-2,4-dioxopyrimidine-5-carboxylate.

NMR spectrum ($CDCl_3$) δ: 2.07(4H, m), 2.17(3H, s), 3.92(3H, s) and (2H, m), 5.90(1H, m), 6.67(1H, d, $J_{HF}=2H_z$), 9.40(1H, broad).

The above syrup, without further purification, is dissolved in 200 ml. of a 1 N aqueous solution of sodium hydroxide and the solution is allowed to stand at room temperature (about 22° C. to 35° C.) for 1 hour. Then, under cooling with ice, the mixture is neutralized with concentrated hydrochloric acid and the yield of 5-fluoro-1-(2-tetrahydrofuryl)-uracil is determined as 62% spectrophotometrically. The solution is adjusted to pH 4 by the addition of acetic acid and adsorbed on a column of activated carbon (20 g.). After the column is washed with water (pH 6-7), the adsorbed substance is eluted by 1 l. of methanol. The methanolic solution is concentrated under reduced pressure to recover 0.74 g. of white solid. This solid is chromatographed on a column of silica gel (25 g., solvent:chloroform-methanol=20/1 (V/V)) and the fractions rich in the contemplated compound are concentrated under reduced pressure to give 0.40 g. of 5-fluoro-1-(2-tetrahydrofuryl)-uracil as a white solid.

NMR spectrum (DMSO-$d_6$) δ: 2.07(4H, m), 3.7–4.5(2H, m), 5.93(1H, m), 7.80(1H, d, $J_{HF}=7H_z$), 11.77(1H, broad).

EXAMPLE 101

In 150 ml. of glacial acetic acid is dissolved 0.94 g. of ethyl 1-(2-tetrahydrofuryl)-1,2,3,4-tetrahydro-2,4-dioxopyrimidine-5-carboxylate and the fluorination is carried out at 18°–24° C. with a gaseous mixture of fluorine (15 V/V %) and nitrogen.

When 2.0 mole equivalents of the gaseous mixture was introduced, the ultraviolet absorption spectrum of the reaction mixture is monitored to confirm that the reaction is complete. The solvent is evaporated under reduced pressure. The resultant colorless syrup is dissolved in 150 ml. of a 1 N aqueous solution of sodium hydroxide and the solution is allowed to stand at room temperature (about 22° C.–35° C.) for 1 hour. Then, under ice-cooling, the reaction mixture is neutralized with concentrated hydrochloric acid. By the ultraviolet absorption spectrum measurement the product is found to be 5-fluoro-1-(2-tetrahydrofuryl)uracil. The yield based on its molecular extinction coefficient is 59%.

UV spectrum $\lambda_{max}^{pH\ 7.0}$ 270 mμ; $\lambda_{max}^{pH\ 13}$ 270 mμ.

EXAMPLE 102

As in Example 100, 2.40 g. (10.0 mmoles) of methyl 1-(2-tetrahydrofuryl)-1,2,3,4-tetrahydro-2,4-dioxopyrimidine-5-carboxylate is fluorinated with 1.7 mole equivalents to fluorine in 200 ml. of acetic acid and the solvent is distilled off under reduced pressure. To the resultant colorless syrup is added 200 ml. of 1 N aqueous solution of sodium hydroxide to effect hydrolysis at 22° to 35° C. for 1 hour. The reaction mixture is cooled with ice and substantially neutralized with 7 ml. of concentrated hydrochloric acid. The yield of 5-fluoro-1-(2-tetrahydrofuryl)uracil based on the ultraviolet absorption data is 62%. The reaction mixture is diluted to 1 liter and desalted by column chromatography on activated carbon (40 g.). Elution is carried out with 3 l. of methanol and the methanol is evaporated under reduced pressure, whereupon 1.40 g. of white solid is obtained. This solid product is dissolved in 250 ml. of water and purified on a column of XAD resin (210 ml. as suspension in water). The by-product, 5-fluorouracil, emerges from the column (1.2 mmoles based on the UV spectrum) as an effluent. The adsorbed desired product is eluted with a mixture of ethanol (17 V/V %) and water. The fractions rich in the desired compound are concentrated under reduced pressure to recover a white solid, which is further recrystallized from ethanol to give 844 mg. of colorless prisms. By the comparisons of thin-layer chromatogram (silica gel, Rf) and ultraviolet absorption spectrum, this crystalline product agrees with an authentic sample of 5-fluoro-1-(2-tetrahydrofuryl)uracil.

UV spectrum: $\lambda_{max}^{pH\ 7.0}$ 270 nm.

EXAMPLE 103

Using 1.6 molar equivalents of fluorine ($F_2/N_2=20$ V/V %), 12.00 g. (50.0 mmoles) of methyl 1-(2-tetrahydrofuryl)-1,2,3,4-tetrahydro-2,4-dioxopyrimidine-5-carboxylate is fluorinated in 500 ml. of acetic acid as in Example 100. The reaction mixture is concentrated under reduced pressure to recover a pale-yellow syrup. This syrup is dissolved in 350 ml. of 1 N aqueous solution of sodium hydroxide and the solution is allowed to stand at 22°–35° C. for 1 hour. The reaction mixture is cooled with ice and substantially neutralized with 12 ml. of concentrated hydrochloric acid. The yield of 5-fluoro-1-(2-tetrahydrofuryl)uracil based on the UV spectral data is 56%. Following addition of 0.7 g. of anhydrous potassium carbonate, the reaction mixture is evaporated to dryness under reduced pressure to recover a brown-colored syrup. The syrup is mixed with 30 g. of anhydrous sodium sulfate and the reaction product is extracted with hot chloroform (7 times, 300 ml. each). The residual solid is dissolved in water and, following addition of 8 ml. of concentrated hydrochloric acid, desalted by passing through a column of 40 g. of activated carbon. The product absorbed on the carbon is eluted with a solution of 10 ml. of concentrated aqueous ammonia in 1.5 l. of methanol. This eluated and the chloroform extract are concentrated under reduced pressure separately, to give 3.0 g. of white solid from the chloroform extract and 4.11 g. of yellowish-tan solid from the methanolic solution (total 7.1 g.). The former crop is chromatographed on silica gel (20 g.; solvent:-chloroform-methanol=20/1(V/V)) to recover 2.77 g. of white solid. Each of the above products is recrystallized from ethanol to obtain total 4.2 g. of 5-fluoro-1-(2-tetrahydrofuryl)uracil as colorless prisms, melting point: 172°–173° C.

UV spectrum $\lambda_{max}^{pH\ 7.0}$ 271 nm.

Elemental analysis, for $C_8H_9FN_2O_3$: Calcd.: C, 48.00; H, 4.53; N, 14.00. Found: C, 48.12; H, 4.43; N, 13.92.

We claim:

1. A compound having the formula:

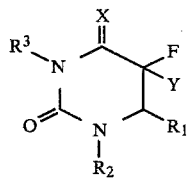

wherein

X is O;

Y is a group of the formula —COOY' wherein Y' is cycloalkyl or alkyl of 1 to 18 carbon atoms, allyl, phenalkyl of 7 to 8 carbon atoms or phenyl, alkylphenyl, alkoxyphenyl, halophenyl, haloalkylphenyl or aminophenyl of 6 to 8 carbon atoms, said alkyl group of 1 to 18 carbon atoms being unsubstituted or substituted by halogen or ethoxy or CN; $R_1$ is a member of the group consisting of (1) hydroxy, (2) etherified hydroxyl selected from the group consisting of alkoxy and cycloalkoxy groups of 1 to 18 carbon atoms, hydroxyethoxy, chloroethoxy, methoxyethoxy, ethoxyethoxy, trifluoroethoxy, allyloxy, cyclohexenyloxy, propargyloxy, 3-butynyloxy, 2-butynyloxy, benzyloxy, p-chlorobenzyloxy, p-fluorobenzyloxy, phenethyloxy and phenoxy, alkylphenoxy, haloalkylphenoxy of 6 to 8 carbon atoms, (3) etherified mercapto corresponding to the etherified hydroxyl as defined above, (4) β-naphthylmercapto and (5) esterified hydroxyl selected from the group consisting of alkanoyloxy or haloalkanoyloxy having 1 to 4 carbon atoms, benzoyloxy, p-methoxybenzoyloxy, p-chlorobenzoyloxy, p-methoxybenzoyloxy, phenylacetyloxy, p-toluenesulfonyloxy and methanesulfonyloxy; and $R_2$ and $R_3$, respectively, are H, lower alkyl or

2. A compound according to claim 1, wherein Y is a group of the formula —COOY' as defined in claim 1; $R_1$ is the etherified hydroxyl as defined in claim 1; $R_2$ is H or

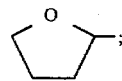

and $R_3$ is H.

3. A compound according to claim 2, wherein Y is a group of the formula —COOY' having 2 to 9 carbon atoms; and $R_1$ is an etherified hydroxyl having 1 to 12 carbon atoms.

4. A compound according to claim 2, wherein Y is a group of the formula —COOY' having 2 to 5 carbon atoms wherein Y' is alkyl having 1 to 4 carbon atoms; $R_1$ is alkoxy having 1 to 8 carbon atoms; and both $R_2$ and $R_3$ are H.

5. Methyl 5-fluoro-6-hydroxy-1,2,3,4,5,6-hexahydro-2,4-dioxopyrimidine-5-carboxylate, according to claim 1.

6. Methyl 5-fluoro-6-methoxy-1,2,3,4,5,6-hexahydro-2,4-dioxopyrimidine-5-carboxylate, according to claim 1.

7. Ethyl 5-fluoro-6-hydroxy-1,2,3,4,5,6-hexahydro-2,4-dioxopyrimidine-5-carboxylate, according to claim 1.

8. Isopropyl 5-fluoro-6-hydroxy-1,2,3,4,5,6-hexahydro-2,4-dioxopyrimidine-5-carboxylate, according to claim 1.

9. n-Butyl 5-fluoro-6-hydroxy-1,2,3,4,5,6-hexahydro-2,4-dioxopyrimidine-5-carboxylate, according to claim 1.

10. sec-Butyl 5-fluoro-6-hydroxy-1,2,3,4,5,6-hexahydro-2,4-dioxopyrimidine-5-carboxylate, according to claim 1.

11. 2-Chloroethyl 5-fluoro-6-hydroxy-1,2,3,4,5,6-hexahydro-2,4-dioxopyrimidine-5-carboxylate, according to claim 1.

12. Methyl 5-fluoro-6-hydroxy-3-methyl-1,2,3,4,5,6-hexahydro-2,4-dioxopyrimidine-5-carboxylate, according to claim 1.

13. Methyl 5-fluoro-1-(2-tetrahydrofuryl)-6-hydroxy-1,2,3,4,5,6-hexahydro-2,4-dioxopyrimidine-5-carboxylate, according to claim 1.

14. Methyl 6-acetoxy-5-fluoro-1,2,3,4,5,6-hexahydro-2,4-dioxopyrimidine-5-carboxylate, according to claim 1.

15. n-Octyl 5-fluoro-6-acetoxy-1,2,3,4,5,6-hexahydro-2,4-dioxopyrimidine-5-carboxylate, according to claim 1.

16. Stearyl 5-fluoro-6-ethoxy-1,2,3,4,5,6-hexahydro-2,4-dioxopyrimidine-5-carboxylate, according to claim 1.

17. 5-Fluoro-6-hydroxy-1,2,3,4,5,6-hexahydro-2,4-dioxopyrimidine-5-carbonitrile, according to claim 1.

18. 3,5-difluoro-6-hydroxy-1,2,3,4,5,6-hexahydro-2,4-dioxopyrimidine-5-carbonitrile.

19. 5-Fluoro-6-acetoxy-1,2,3,4,5,6-hexahydro-2,4-dioxopyrimidine-5-carbonitrile, according to claim 1.

20. Methyl 5-fluoro-6-cyclohexyloxy-1,2,3,4,5,6-hexahydro-2,4-dioxopyrimidine-5-carboxylate, according to claim 1.

21. Methyl 5-fluoro-6-n-octyloxy-1,2,3,4,5,6-hexahydro-2,4-dioxopyrimidine-5-carboxylate, according to claim 1.

22. n-Butyl 5-fluoro-6-n-butoxy-1,2,3,4,5,6-hexahydro-2,4-dioxopyrimidine-5-carboxylate, according to claim 1.

23. Ethyl 5-fluoro-6-ethoxy-1,2,3,4,5,6-hexahydro-2,4-dioxopyrimidine-5-carboxylate, according to claim 1.

24. Ethyl 5-fluoro-6-allyloxy-1,2,3,4,5,6-hexahydro-2,4-dioxopyrimidine-5-carboxylate, according to claim 1.

25. Ethyl 5-fluoro-6-propargyloxy-1,2,3,4,5,6-hexahydro-2,4-dioxopyrimidine-5-carboxylate, according to claim 1.

26. Ethyl 5-fluoro-6-tert-butyloxy-1,2,3,4,5,6-hexahydro-2,4-dioxopyrimidine-5-carboxylate, according to claim 1.

27. Ethyl 5-fluoro-6-n-octadecyloxy-1,2,3,4,5,6-heaxhydro-2,4-dioxopyrimidine-5-carboxylate, according to claim 1.

28. Ethyl 5-fluoro-6-neopentyloxy-1,2,3,4,5,6-hexahydro-2,4-dioxopyrimidine-5-carboxylate, according to claim 1.

29. Isopropyl 5-fluoro-6-isopropyloxy-1,2,3,4,5,6-hexahydro-2,4-dioxopyrimidine-5-carboxylate, according to claim 1.

30. sec-Butyl 5-fluoro-6-sec-butyloxy-1,2,3,4,5,6-hexahydro-2,4-dioxopyrimidine-5-carboxylate according to claim 1.

31. n-Octyl 5-fluoro-6-n-octyloxy-1,2,3,4,5,6-hexahydro-2,4-dioxopyrimidine-5-carboxylate, according to claim 1.

32. Ethyl 5-fluoro-6-ethylthio-1,2,3,4,5,6-hexahydro-2,4-dioxopyrimidine-5-carboxylate, according to claim 1.

33. Ethyl 5-fluoro-6-tert-butylthio-1,2,3,4,5,6-hexahydro-2,4-dioxopyrimidine-5-carboxylate, according to claim 1.

34. Ethyl 5-fluoro-6-cyclohexylthio-1,2,3,4,5,6-hexahydro-2,4-dioxopyrimidine-5-carboxylate, according to claim 1.

35. Ethyl 5-fluoro-6-n-decylthio-1,2,3,4,5,6-hexahydro-2,4-dioxopyrimidine-5-carboxylate, according to claim 1.

36. Ethyl 5-fluoro-6-n-octadecylthio-1,2,3,4,5,6-hexahydro-2,4-dioxopyrimidine-5-carboxylate, according to claim 1.

37. Methyl 5-fluoro-6-phenylthio-1,2,3,4,5,6-hexahydro-2,4-dioxopyrimidine-5-carboxylate, according to claim 1.

38. n-Octyl 5-fluoro-6-ethoxy-1,2,3,4,5,6-hexahydro-2,4-dioxopyrimidine-5-carboxylate, according to claim 1.

39. n-Octyl 5-fluoro-6-hydroxy-1,2,3,4,5,6-hexahydro-2,4-dioxopyrimidine-5-carboxylate, according to claim 1.

40. Methyl 6-benzoyloxy-5-fluoro-1,2,3,4,5,6-hexahydro-2,4-dioxopyrimidine-5-carboxylate, according to claim 1.

41. Methyl 6-benzyloxy-5-fluoro-1,2,3,4,5,6-hexahydro-2,4-dioxopyrimidine-5-carboxylate, according to claim 1.

42. Ethyl 6-benzylthio-5-fluoro-1,2,3,4,5,6-hexahydro-2,4-dioxopyrimidine-5-carboxylate, according to claim 1.

43. Ethyl 6-allylthio-5-fluoro-1,2,3,4,5,6-hexahydro-2,4-dioxopyrimidine-5-carboxylate, according to claim 1.

44. Ethyl 5-fluoro-6-β-naphthylthio-1,2,3,4,5,6-hexahydro-2,4-dioxopyrimidine-5-carboxylate, according to claim 1.

45. Ethyl 5-fluoro-6-(2,2,2-trifluoro)ethoxy-1,2,3,4,5,6-hexahydro-2,4-dioxopyrimidine-5-carboxylate, according to claim 1.

46. Methyl 5-fluoro-6-ethoxy-1,2,3,4,5,6-hexahydro-2,4-dioxopyrimidine-5-carboxylate, according to claim 1.

47. Ethyl 5-fluoro-6-methoxy-1,2,3,4,5,6-hexahydro-2,4-dioxopyrimidine-5-carboxylate, according to claim 1.

48. Ethyl 5-fluoro-6-isopropoxy-1,2,3,4,5,6-hexahydro-2,4-dioxopyrimidine-5-carboxylate, according to claim 1.

49. Methyl 5-fluoro-6-butoxy-1,2,3,4,5,6-hexahydro-2,4-dioxopyrimidine-5-carboxylate, according to claim 1.

50. Ethyl 5-fluoro-6-butoxy-1,2,3,4,5,6-hexahydro-2,4-dioxopyrimidine-5-carboxylate, according to claim 1.

51. Ethyl 5-fluoro-6-isobutoxy-1,2,3,4,5,6-hexahydro-2,4-dioxopyrimidine-5-carboxylate, according to claim 1.

52. Ethyl 5-fluoro-6-sec-butoxy-1,2,3,4,5,6-hexahydro-2,4-dioxopyrimidine-5-carboxylate, according to claim 1.

53. Ethyl 5-fluoro-6-benzyloxy-1,2,3,4,5,6-hexahydro-2,4-dioxopyrimidine-5-carboxylate, according to claim 1.

54. Ethyl 5-fluoro-6-phenoxy-1,2,3,4,5,6-hexahydro-2,4-dioxopyrimidine-5-carboxylate, according to claim 1.

55. Methyl 5-fluoro-6-butylthio-1,2,3,4,5,6-hexahydro-2,4-dioxopyrimidine-5-carboxylate, according to claim 1.

56. Ethyl 5-fluoro-6-phenylthio-1,2,3,4,5,6-hexahydro-2,4-dioxopyrimidine-5-carboxylate, according to claim 1.

57. 5-Fluoro-6-ethoxy-1,2,3,4,5,6-hexahydro-2,4-dioxopyrimidine-5-carbonitrile, according to claim 1.

58. Ethyl 5-fluoro-6-octyloxy-2,4-dioxo-1,2,3,4,5,6-hexahydropyrimidine-5-carboxylate, according to claim 1.

59. Ethyl 5-fluoro-t-6-octyloxy-1,2,3,4,5,6-hexahydro-2,4-dioxopyrimidine-r-5-carboxylate, according to claim 1.

60. Ethyl 5-fluoro-c-6-octyloxy-1,2,3,4,5,6-hexahydro-2,4-dioxopyrimidine-r-5-carboxylate, according to claim 1.

61. Ethyl 6-acetoxy-5-fluoro-1,2,3,4,5,6-hexahydro-2,4-dioxopyrimidine-5-carboxylate, according to claim 1.

62. Methyl 6-acetoxy-5-fluoro-1-(2-tetrahydrofuryl)-1,2,3,4,5,6-hexahydro-2,4-dioxopyrimidine-5-carboxylate, according to claim 1.

* * * * *